US010350259B2

(12) United States Patent
Ilag et al.

(10) Patent No.: US 10,350,259 B2
(45) Date of Patent: Jul. 16, 2019

(54) SUGAR CANE DERIVED EXTRACTS AND METHODS OF TREATMENT

(71) Applicant: The Product Makers (Australia) PTY LTD, Keysborough, Victoria (AU)

(72) Inventors: Leodevico Luna Ilag, Balwyn (AU); Timothy Peter Ellis, Glen Waverley (AU); Alison Grace Wright, Glen Iris (AU)

(73) Assignee: THE PRODUCT MAKERS (AUSTRALIA) PTY LTD, Keysborough, Victoria (AU)

( * ) Notice: Subject to any disclaimer, the term of this patent is extended or adjusted under 35 U.S.C. 154(b) by 536 days.

(21) Appl. No.: 14/912,339

(22) PCT Filed: Aug. 15, 2014

(86) PCT No.: PCT/AU2014/050187
§ 371 (c)(1),
(2) Date: Feb. 16, 2016

(87) PCT Pub. No.: WO2015/021512
PCT Pub. Date: Feb. 19, 2015

(65) Prior Publication Data
US 2016/0193275 A1 Jul. 7, 2016

(30) Foreign Application Priority Data

Aug. 16, 2013 (AU) .................................. 2013903105

(51) Int. Cl.
| | | |
|---|---|---|
| A61K 36/00 | (2006.01) |
| A61K 36/899 | (2006.01) |
| A61K 31/05 | (2006.01) |
| A23L 2/52 | (2006.01) |
| A61K 31/7004 | (2006.01) |
| A61K 31/7016 | (2006.01) |
| A23L 33/105 | (2016.01) |

(52) U.S. Cl.
CPC .............. *A61K 36/899* (2013.01); *A23L 2/52* (2013.01); *A23L 33/105* (2016.08); *A61K 31/05* (2013.01); *A61K 31/7004* (2013.01); *A61K 31/7016* (2013.01)

(58) Field of Classification Search
CPC ...................................................... A61K 36/00
See application file for complete search history.

(56) References Cited

U.S. PATENT DOCUMENTS

| | | | |
|---|---|---|---|
| 2,170,713 A | 8/1939 | Fattinger |
| 2,342,162 A | 2/1944 | Musher |
| 3,619,293 A | 11/1971 | Niimi et al. |
| 3,975,205 A | 8/1976 | Munir et al. |
| 4,101,338 A | 7/1978 | Rapaport et al. |
| 4,102,646 A | 7/1978 | Sleeter |
| 4,111,714 A | 9/1978 | Hippehen et al. |
| 4,116,712 A | 9/1978 | Othmer |
| 4,333,770 A | 7/1982 | Neuzil et al. |
| 4,359,430 A | 11/1982 | Heikkila et al. |
| 4,404,037 A | 9/1983 | Broughton |
| 4,523,959 A | 6/1985 | Exertier |
| 4,523,999 A | 6/1985 | Toyoshi et al. |
| 5,096,594 A | 3/1992 | Rabinowitz |
| 5,127,957 A | 7/1992 | Heikkila et al. |
| 5,252,136 A | 10/1993 | Desforges et al. |
| 5,382,294 A | 1/1995 | Rimedio et al. |
| 5,384,035 A | 1/1995 | Smolnik et al. |
| 5,482,631 A | 1/1996 | Saska et al. |
| 5,556,546 A | 9/1996 | Tanimura et al. |
| 5,578,336 A | 11/1996 | Monte |
| 5,663,156 A | 9/1997 | Granja et al. |
| 5,955,269 A | 9/1999 | Ghai et al. |
| 6,093,326 A | 7/2000 | Heikkila et al. |
| 6,099,654 A | 8/2000 | Kaneko et al. |
| 6,217,664 B1 | 4/2001 | Baniel |
| 6,372,049 B1 | 4/2002 | Shimanskaya et al. |
| 6,406,547 B1 | 6/2002 | Donovan et al. |
| 6,406,548 B1 | 6/2002 | Donovan et al. |
| 6,475,390 B1 | 11/2002 | Durham et al. |
| 6,528,099 B1 | 3/2003 | Gard et al. |
| 6,630,672 B1 | 10/2003 | Brotherton et al. |
| 6,723,369 B2 | 4/2004 | Burgess |
| 6,777,397 B2 | 8/2004 | Zehner et al. |
| 6,869,625 B2 | 3/2005 | Gupta et al. |
| 6,885,003 B1 | 4/2005 | Dubernet |
| 7,015,339 B2 | 3/2006 | Khare et al. |
| 7,150,885 B2 | 12/2006 | Araki et al. |
| 7,312,199 B2 | 12/2007 | Burdick et al. |
| 8,138,162 B2 | 3/2012 | Kannar |

(Continued)

FOREIGN PATENT DOCUMENTS

| | | |
|---|---|---|
| AU | 2011/204847 | 8/2001 |
| CA | 2053412 | 4/1992 |

(Continued)

OTHER PUBLICATIONS

Guimaraes et al, Antioxidant activity of sugar molasses, including protective effect against DNA oxidative damage. Journal of Food Science (2007), vol. 72, No. 1, pp. C39-C43 (Year: 2007).*

(Continued)

*Primary Examiner* — Qiuwen Mi
(74) *Attorney, Agent, or Firm* — Brian C. Trinque; Lathrop Gage LLP

(57) ABSTRACT

The invention relates to extracts produced from sugar cane processing stream products having desirable properties and health benefits. More particularly the invention relates to sugar cane derived extracts obtained from molasses, methods of producing the extracts, and uses of the extracts for management of insulin resistant conditions or subjects predisposed to such conditions, such as type 2 diabetes. The sugar cane derived extracts of the invention are enriched in polyphenols and the administration of the sugar cane derived extract regulates postprandial glucose response and insulin response and lowering those responses, to avoid the subject becoming hypoglycaemic.

23 Claims, 13 Drawing Sheets

(56) References Cited

U.S. PATENT DOCUMENTS

| | | |
|---|---|---|
| 2001/0001178 A1 | 5/2001 | Donovan et al. |
| 2001/0001956 A1 | 5/2001 | Hyoky et al. |
| 2002/0082287 A1 | 6/2002 | Harada et al. |
| 2002/0150652 A1 | 10/2002 | Antila et al. |
| 2002/0169311 A1 | 11/2002 | Paananen et al. |
| 2002/0187219 A1 | 12/2002 | Yang et al. |
| 2002/0197380 A1 | 12/2002 | Mantius et al. |
| 2003/0082287 A1 | 5/2003 | Wolt et al. |
| 2003/0124170 A1 | 7/2003 | Gallaher et al. |
| 2003/0124208 A1 | 7/2003 | Makino et al. |
| 2003/0147978 A1 | 8/2003 | Araki et al. |
| 2003/0161903 A1 | 8/2003 | Konishi et al. |
| 2003/0165574 A1 | 9/2003 | Ward et al. |
| 2003/0198694 A1 | 10/2003 | Chou |
| 2003/0232763 A1 | 12/2003 | Jia |
| 2004/0001862 A1 | 1/2004 | Xiu |
| 2004/0006222 A1 | 1/2004 | Paananen et al. |
| 2004/0006223 A1 | 1/2004 | Karki et al. |
| 2004/0052915 A1 | 3/2004 | Carlson et al. |
| 2004/0060868 A1 | 4/2004 | Heikkila et al. |
| 2004/0081734 A1 | 4/2004 | Lang |
| 2004/0097429 A1 | 5/2004 | Nieuwenhuizen et al. |
| 2004/0131749 A1 | 7/2004 | Grabiel et al. |
| 2004/0151815 A1 | 8/2004 | Jensen et al. |
| 2004/0191336 A1 | 9/2004 | Hilaly et al. |
| 2004/0197380 A1 | 10/2004 | Wolf et al. |
| 2005/0175674 A1 | 8/2005 | Lang et al. |
| 2005/0181074 A1 | 8/2005 | Watson et al. |
| 2005/0214419 A1 | 9/2005 | Aberle et al. |
| 2006/0003029 A1 | 1/2006 | Nash et al. |
| 2006/0121158 A1 | 6/2006 | Ferruzzi et al. |
| 2006/0147556 A1 | 6/2006 | Brewer |
| 2007/0014912 A1 | 1/2007 | Mazza et al. |
| 2007/0158269 A1 | 7/2007 | Paananen et al. |
| 2007/0160698 A1 | 7/2007 | Waga et al. |
| 2007/0166246 A1 | 7/2007 | Takagaki et al. |
| 2007/0178175 A1 | 8/2007 | Matsubara et al. |
| 2007/0190209 A1 | 8/2007 | Sinnott |
| 2008/0286254 A1 | 11/2008 | Sakamoto et al. |
| 2009/0047368 A1 | 2/2009 | Numata et al. |
| 2009/0053333 A1 | 2/2009 | Sambanthamurthi et al. |
| 2009/0281057 A1 | 11/2009 | Bhaskaran et al. |
| 2010/0112099 A1 | 5/2010 | Tripp et al. |
| 2010/0130422 A1 | 5/2010 | Bernaert et al. |
| 2010/0166851 A1 | 7/2010 | Dallas et al. |
| 2010/0184666 A1 | 7/2010 | Bernaert et al. |
| 2010/0196549 A1 | 8/2010 | Rivera et al. |
| 2014/0315993 A1 | 10/2014 | Kannar |

FOREIGN PATENT DOCUMENTS

| | | |
|---|---|---|
| CA | 2420881 | 9/2001 |
| CN | 1484974 | 3/2004 |
| CN | 1685929 | 10/2005 |
| CN | 101317850 | 12/2008 |
| DE | 3232693 A1 | 7/1983 |
| EP | 1362517 | 11/2003 |
| EP | 1362919 | 11/2003 |
| EP | 1447013 | 8/2004 |
| EP | 1447014 | 8/2004 |
| EP | 1 466609 | 10/2004 |
| FR | 2797688 | 2/2001 |
| FR | 2929852 | 10/2009 |
| JP | S 58144382 | 8/1963 |
| JP | S 5359044 | 5/1978 |
| JP | S 59-020223 | 2/1984 |
| JP | S 61-69727 | 4/1986 |
| JP | S 61-83130 | 4/1986 |
| JP | S 61-139400 | 6/1986 |
| JP | S 61-265068 | 11/1986 |
| JP | S 61-268200 | 11/1986 |
| JP | S 62-126951 | 6/1987 |
| JP | S 63-207400 | 8/1988 |
| JP | H 01244000 | 9/1989 |
| JP | H 0220300 | 1/1990 |
| JP | H 03145424 | 6/1991 |
| JP | H 04320691 | 11/1992 |
| JP | H 05211900 | 8/1993 |
| JP | H 0662798 | 3/1994 |
| JP | H 0840912 | 2/1996 |
| JP | H 0925290 | 1/1997 |
| JP | H 1175758 | 3/1999 |
| JP | H 11318405 | 11/1999 |
| JP | 2000-032954 | 2/2000 |
| JP | 2000-0297045 | 10/2000 |
| JP | 2001-200250 | 3/2001 |
| JP | 2001-112439 | 4/2001 |
| JP | 2001-131080 | 5/2001 |
| JP | 2001-302533 | 10/2001 |
| JP | 2002-020306 | 1/2002 |
| JP | 2002-161046 | 6/2002 |
| JP | 2003-063975 | 3/2003 |
| JP | 2003-116486 | 4/2003 |
| JP | 2003-137803 | 5/2003 |
| JP | 2003137803 A * | 5/2003 |
| JP | 2004-065018 | 3/2004 |
| JP | 2004-075612 | 3/2004 |
| JP | 2004-331512 | 11/2004 |
| JP | 2005-278407 | 10/2005 |
| JP | 2005-343843 | 12/2005 |
| JP | 2006-028020 | 2/2006 |
| JP | 2006-131578 | 5/2006 |
| JP | 2006-321772 | 11/2006 |
| JP | 2007-043940 | 2/2007 |
| JP | 2007-063221 | 3/2007 |
| JP | 2008-044872 | 2/2008 |
| JP | 2008-222656 | 9/2008 |
| JP | 2009-298769 | 12/2009 |
| KR | 100894911 | 4/2009 |
| KR | 20090063794 | 6/2009 |
| RU | 2048847 | 11/1995 |
| WO | WO 89/01295 | 3/1988 |
| WO | WO 1994/12057 | 6/1994 |
| WO | WO 1997/049734 | 12/1997 |
| WO | WO2001/036690 | 5/2001 |
| WO | WO 2001/078629 | 10/2001 |
| WO | WO 2002/014477 | 2/2002 |
| WO | 2002/020112 A1 | 3/2002 |
| WO | WO 02/078469 | 10/2002 |
| WO | WO 2003/074144 | 9/2003 |
| WO | WO 2003/074145 | 9/2003 |
| WO | WO 2003/075685 | 9/2003 |
| WO | WO 2003/099309 | 12/2003 |
| WO | WO 2004/014159 | 2/2004 |
| WO | WO 2005/006891 | 1/2005 |
| WO | WO 2005/052195 | 6/2005 |
| WO | WO 2005/089066 | 9/2005 |
| WO | WO 2005/105852 | 11/2005 |
| WO | WO 2005/117608 | 12/2005 |
| WO | WO 2006/014028 | 2/2006 |
| WO | WO 2006/052007 | 5/2006 |
| WO | WO 2006/128253 | 12/2006 |
| WO | WO 2006/128259 | 12/2006 |
| WO | WO 2007/041817 | 4/2007 |
| WO | WO 2008/034180 | 3/2008 |
| WO | WO 2008/142178 | 11/2008 |
| WO | WO 98/55658 | 4/2009 |
| WO | WO 2009/046492 | 4/2009 |
| WO | WO 2009/136219 | 11/2009 |
| WO | WO 2010/094837 | 8/2010 |
| WO | WO 2010/094860 | 8/2010 |
| WO | WO 2010/118474 | 10/2010 |
| WO | WO 2012/106761 | 8/2012 |

OTHER PUBLICATIONS

Fahey et al. (1976) "Influence of molasses lignin-hemicellulose fractions in rat nutrition," The Journal of Nutrition. 106(10):1447-1451.

Klasing et al. (1985) "Biological activity of phenolic compounds. Hepatic cytochrome P-450, cytochrome b5, and NADPH cytochrome c reductase in chicks and rats fed phenolic monomers, polymers, and glycosides," Proc. Soc. Exp. Biol. Med. 179:529-538.

(56) References Cited

OTHER PUBLICATIONS

"Gekkan Food Chemical," 2001 pp. 72-81, vol. 17 No. 10 (English translation of abstract only).
"Shokuhin to Kaihatus," 2000, pp. 15-18, vol. 35 No. 6 (English translation of abstract only).
Aijun, Dong et al., "A Functional Oliogsaccharide in Sugar Beet—Raffinose." China Beet & Sugar, No. 3, Sep. 2001, pp. 24-26.
Altukhov et al., 2004, Human Physiol. 30(2):216-223.
Anderson, 2008, Proc. Nutrition Soc. 67:48-53.
Baba et al., 2005, Eur. J. Nutr. 44:1-9.
Badescu et al, 2005, Rom. J. Physiol. 42:1-4, pp. 103-120.
Balasubramanian et al., 2010, Carcinogenesis 31(3):496-503.
Banini et al., 2006, Nutrition 22:1137-1145.
Basu et al., 2010, J. Nutr. 140:1582-1587.
Bento et al, 1997, SIT Poster #722 Publ. Techn. Papers Proc. Ann. Meet Sugar industry Technologiests 56:383-392 "Gel Permeation Chromatography of Sugar Materials Using . . . ".
Bento et al., 1998, Carbohydrate Polymers 37:257-261.
Bento et al., 1997, Intl. Sugar J. 99(1187 Suppl.):555-562.
Berhow et al., 2000, Mutation Res. 448:11-22.
Bray et al., "Current and Potential Drugs for Treatment of Obesity" 1999, Endocrine Rev 20(6):805-875.
Brown et al, 2009, Br. J. Nutr. 101 :886-894.
Bureau of Sugar Experiment Stations (BSES), "Laboratory Manual for Australian Sugar Mills," Apr. 2001, 2 pages; vol. 2, Method 33, BSES Brisbane.
Burkon et al., 2008, Mol. Nutr. Food Res. 52:549-557.
Casey et al., "Comparision of the Concentrations of Phenolic Constituents in Cane Sugar Manufacturing Products with their Antioxidant Activities", J. Agric. Food Chem., 2006, pp. 7270-7276, vol. 54.
Chajuss, 2004, "Soy Molasses: Processing and Utilization as a Functional Food," In: Soybeans as Functional Foods and ingredients, Liu et al., Eds.
Clarke et al, "Polyfructose: A New Microbial Polysaccharide," In: Carbohydrates as Organic Raw Materials, Lichtenthaler, Ed., VCH. Weinheim, 1990.
Coca et al, 2005, Chemosphere 60:1408-1415.
Dallas et al., 2008, Phytomedicine 15:783-792.
Dal-Pan et al., 2010, BMC Physiol. 10:11.
Edye et al., 1998, "The Fate of Soluble Sugarcane Polysaccharides in Sugar Manufacture," Poster.
Fernandes et al., 2009, Talanta 79:222-228.
Frank et al., 2009, J. Nutr. 139:58-62.
Fujita et al., 2000, Abstract AGFD-086, Book of Abstracts, 219th ACS National Meeting, San Francisco, CA, Amer. Chem. Soc., Washington, DC.
Fukino et al, 2005, J. Nutr. Sci. Vitarninol. 51:335-342.
Fukino et al, 2008, Eur. J. Clin. Nutr. 62:953-960.
Goossens, G.H.; "Possible Involvement of the Adipose Tissue Renin-Angiotensin System in the Pathophysiology of Obesity and Obesity-Related Disorders" et al., 2003, Obesity Rev. 4:43-55.
Han et al., "Anti-Obesity Action of Salix matsudana Leaves (Part 1). Anti-Obesity Action by Polyphenols of Salix Matsudana in High Fat-Diet Treated Rodent Animals"; 2003, Phytotherapy Res. 17:1188-1194.
Hangyal, 1969, Cukoripar 22(5):183-186 (Abstract only; HCAPLUS database record No. 1970:123241).
Hatano et al, 2008, Chemosphere 71 :1730-1737.
Hollis et al., 2009, J. Amer. Coll. Nutr. 28(5):574-582.
Hu et al, 2006, Zhongguo Unchuang Kangfu 10(43):79-81 (Abstract Only).
Ishikura et al, 2008, Jap. Pharmacol Therapeut. 36(10):931-939 (Abstract Only).
Islam, 2008, Z. Naturforsch. 63c:233-240.
Jacome et al., 2009, Alim. Nutr. 20(2): 185-190.
Kajimoto et al., "Tea Catechins with a Galloyl Moiety Reduce Body Weight and Fat" 2005, J. Health Sci. 51(2):161-171.
Kantachote, 2009, Electr. J. Biotechnol. 12(3):12.
Khan et al., 2010, 61(15):4185-4196.
Kim et al., "Antioxidant capacity of phenolic phytochemicals from various cultivars of plums," Food Chemistry, 2003; pp. 321-326, 81.
Kishihara et al., 1986, Kagaku Kogaku Ronbunshu 12(2):1 99-205 (Abstract Only).
Kita et al., 2004, BioFactors 22:259-263.
Koge K. et al., Antioxidants and Other Functional Extracts from Sugarcane, Chapter 15, 411-431, (2005).
Kovacs et al., 2004, Br. J. Nutr. 91 :431-437.
Kumar et al., "Effect of Long Term Feeding of Urea Molasses Liquid Diet (UMLD) on Ovarian Activity in Crossbred Heifers", 1998, Indian Vet. Med. J. 22:185-188.
Lee et al., 2008, Hanguk Kikpum Yongyang Kwahak Hoechi 37(5):561-570 (Abstract Only).
Loke et al., 2010, Arterioscler. Thrornb. Vasc. Biol. 30:749-757.
Machowetz et al, 2008, Horrn. Metab. Res. 40:697-701.
Mantovani et al, 2004, Cancer Epidemiol. Biomarkers Prey. 13 (10):1651-1659.
Mantovani et al., 2008, Nutrition 24:305-313.
Mantovani et al., 2006, Cancer Epidemiol. Biomarkers Prev. 15:•1030-1034.
Mehra et al.,"Effect of Restricted and Ad libilum Feeding of Urea Molasses Liquid Diet (UMLD) on the Performance of Adult Cross-bred Cattle" 1998, Asian-Australasian J Animal Sci:11(1):30-34.
Melby et al. , 2007, Daizu Tanpakushitsu Kenkyu 9:-138-146 (Abstract Only).
Nagao et al, 2009, Jap. Pharmacol. Therapeut. 37(4):333-344 (Abstract Only).
Nagasako-Akazome et al., 2007, J. Oleo Sci. 56(8):417-428.
Nakamura et al., 2007, Jap. Pharmacol. Therapeut. 35(6):661-67•1 (Abstract Only).
Nakamura et al., 2008, Jap. Pharmacol. Therapeut. 36(4):347-357 (Abstract Only).
Ochiai et al, 2009, Hypertension Res. 32:969-974.
Olthof et. al., 2000, "Metabolism of Chlorogenic Acid, Querctein-3-rutinoside and . . . " In: Spec. Publ. Royal Soc. Chem: 255 Dietary Anticarcinogens and Antimutagens, pp. 73-75.
Onimawo et al., 2010, African J. Food Agric. Nutr. Develop. 10(5): May 2010, pp. 2570-2586, ISSN 1684 5374.
Palfi et al., 2009, J. Nutr. Biochem. 20:418-425.
Pasman et al. "Effect of two breakfasts, different in carbohydrate composition on hunger and satiety and mood in healthy men", International Journal of Obesity 27:663-668 (2003).
Payet et al., "Comparision of the Concentrations of Phenolic Constituents in Cane Sugar Manufacturing Products with their Antioxidant Activities", J Agric. Food Chem., 2006, pp. 7270-7276, vol. 54.
Patton et al., "Use of a spectrophotometric bioassay for determination of microbial sensitivity to Manuka honey", Journal of Microbiological Methods, 2006, pp. 84-95, vol. 64.
Pena et al., 2003, Chernosphere 51 :893-900.
Qu et al., 2007, J. Clin. Rehabil. Tiss. Eng. Res. 11 (43):8805-8808.
Rosenberg et al., 1956, "Response of Growing and Mature Pullets to Continuous Feeding of Cane Final Molasses," Hawaii Agricultural Experiment Station Technical Paper No. 349.
Schoen et al., 2009, Nutrition 25:499-505.
Shore et al., 1984, Sugar Technol. Rev. 12:1-99.
Sies et al., 2005, J. Nutrition 135(5):969-972.
Simonetti et al, 2001, Meth. Enzymol. 335:122-130.
Singleton et al., "Colorimetry of total phenolics with phosphomolybdic-phosphotungstic acid reagents," Am. J. Enol. Vitic., 1965, pp. 144-158, 16.
Staunton et al., "Development of an online bagasse analysis system using NIR spectroscopy," International Sugar Journal, 2007, pp. 482-488, 109.
Staunton et al., "On-line can analysis by near infra-red spectroscopy," Proc. Aust. Soc. Sugar Cane Technol., 1999, pp. 20-27, 21.
Stracke et al., 2010, Eur. J. Nutr. 49:301-310.
Tominaga et al., 2006, J. Health Sci. 52(6):672-683.
Vercellotti et al., 1998, Membrane Separation Chemistry in Sugar Processing Applications, Proceedings of the Conference on Sugar Processing Research , Savannah, GA, pp. 248-28.
Vercellotti et al., 1996, Proc. Conf. Sugar Processing Res., SPRI, New Orleans, 321-349.

(56) References Cited

OTHER PUBLICATIONS

Vercellotti et al., 1998. SIT Paper 727, Sugar Industry Technologist Annual Meeting, Marseille France, pp. 49-78.
Wachowicz, 1978, Gazeta Cukrownicza 86: 1 25-127 (Abstract Only: HCAPLUS database record No. 1978:548469).
Wang et al., 2008, Carbohydrate Polymers 74:127-132.
Winter et al., 1992, J. Exp. Mar. Biol. Ecol., 155:263-277.
Wu et al., 2002, Huanjing Wuran Yu Fangzhi 24(1):13-18 (Abstract Only; HCAPLUS database record No. 2002:439963).
Wu et al., 2005, Carcinogenesis 26(5):976-980.
Yinfa, Zhang et al., "Application of Food Glycemic Index in Diabetes Nutrition Education," Acta Nutrirnenta Sinica, Sep. 2003. vol. 25, No. 3, pp. 248-251.
Yoshikawa M. et al., "Medicinal Foodstuffs, III and IV from the Roota of Beta Vulgaris L. (Chenopodiacae)," Chemical and Pharmaceutical Bulletin, Pharmaceutical Society of Japan, Tokyo, JP; vol. 44, No. 6, Jan. 1, 1996, p. 1212-1217.
Zemel, M. "Regulation of Adiposity and Obesity Risk by Dietary Calcium: Mechanisms and Implications," 2002, J. Am. Coll. Nutr. 21(2):1 46S-151S.
Zhang et al, 2009, Zhongguo Difangbingxue Zazhi 28(4):38.1-385 (Abstract Only}.
Zhang et al., 2007, Can. J. Physiol. Pharmacol. 85:1116-1123.
Zheng et al., "Anti-Obesity Effects of the Three Major Components of Green Tea, Catechins, Caffeine and Theanine, in Mice". Anti 2004, In Vivo 18:55-62.
Zielinska-Przyjemska et al., 2005, Polski Merkuriusz 19(109):41-47 (.Abstract Only).
Zieunska-Przyjemska et al.. 2007 Acta Sci. Pol., Technol. Aliment. 6 (3):75-87.

\* cited by examiner

| Average values: | | | | | Typical values: | | |
|---|---|---|---|---|---|---|---|
| Component: | Molasses extract | | Mill molasses | | Component: | Molasses extract | Mill molasses |
| | As is: | Dry basis: | As is: | Dry basis: | | | |
| Moisture, g/100g | 38.4 | - | 15.8 | | Brix (°Bx, refrac) | Min 62 | Not tested |
| Energy, (calc) kJ/100g | 946 | 1536 | 1250 | 1485 | Density, g/ml | 1.29 – 1.39 | 1.45 (est) |
| Protein (N x 6.25, g/100g) | 2.0 | 3.25 | 4.2 | 5.0 | Viscosity | | Not tested |
| Fat, g/100 g | 0.9 | 1.46 | 1.1 | 1.3 | 20°C, 60rpm, spindle LV2 | 88 cPs | |
| Sucrose, g/100 g | 29.3 | 47.6 | 38 | 45.1 | 45°C, 60rpm, spindle LV2 | 31 cPs | |
| Glucose, g/100 g | 5.4 | 8.8 | 4.6 | 5.5 | Colour, ICUMSA units | 47000 | Not tested |
| Fructose, g/100 g | 6.0 | 9.7 | 6.2 | 7.4 | Glycemic index value | 45 ± 4 | Not tested |
| Total sugars, g/100 g | 40.7 | 66.1 | 49 | 58 | Aw | 0.85 | Not tested |
| Sodium, mg/100 g | 50 | 81 | 62 | 74 | pH | 5.3 – 5.9 | Not tested |
| Soluble dietary fibre, g/100g | 0.3 | 0.5 | 1.7 Total fibre - 1.9 | 2.0 Total fibre - 2.3 | Polyphenols, mg CE/100g | min 1150 (1850 dry basis) | avg 1970 (2340 dry basis) |
| Ash, g/100g | 6.1 | 9.9 | 9.0 | 10.7 | Flavonoids, mg/100g | 270 (440 db) | 640 (750 db) |
| Total carbohydrate (by difference, g/100g) | 52.3 | 84.9 | 68 | 81 | ORAC Value Vit E Equiv (total), μmol/100g | 18,000 (29,000 db) | 44,000 (52,250 db) |
| | | | | | Shelf life/Best Before | 12 months | Not tested |
| Minerals (avg values): | Molasses extract | | Mill molasses | | | Molasses extract | Mill molasses |
| | As is: | Dry basis: | As is: | Dry basis: | | As is: Dry basis: | As is: Dry basis: |
| Calcium, mg/kg | 5450 | 8850 | 7500 | 8900 | Manganese, mg/kg | 45   73 | 62   74 |
| Iron, mg/kg | 89 | 144 | 170 | 200 | Potassium, mg/kg | 24,500   40,000 | 30,000   35,600 |
| Magnesium, mg/kg | 2000 | 3250 | 2700 | 3200 | Zinc, mg/kg | 3.3   5.4 | 6.3   7.5 |

| Food tested | Ingredients<br>Test products also contain filtered molasses concentrate, FMC | Approximate Composition, g/100g: | | | g CHO/ 100g | Portion tested | Extract added / 100g | Extract/ 100 g CHO |
|---|---|---|---|---|---|---|---|---|
| | | Protein | Fat | Moisture | | | | |
| White bread | Flour, water, butter, salt, yeast, sugar | 8 | 3 | 37 | C : 41.3<br>T : 41.4 | 121.1g<br>120.8 | -<br>2.50 g | -<br>6.04g |
| Glucose syrup | Glucose syrup | 0.1 | 0 | 30 | C : 81.4<br>T : 79.2 | 61.4g<br>63.1g | -<br>3.5g | -<br>4.42g |
| Fruit flavoured beverage | Water, sugar, citric acid, flavour, colour, sodium benzoate, sodium metabisulphite | 0 | 0 | 93.5 | C : 6.5<br>T : 6.1 | 769.2g<br>819.7g | -<br>0.22 g/ 100ml | -<br>3.6g |
| Energy bar | Soy protein isolate, peanut butter, corn syrup, inulin, fructose, sugar, rice starch, wheat germ, salt, high-fructose corn syrup, whey, vitamins, flavours, preservatives. Coating: sugar, palm kernel oil, cocoa, whey, non-fat milk, soy lecithin, flavours and preservatives. | 11 | 13 | 19 | C : 51.7<br>T : 49.9 | 96.7g<br>100.2g | -<br>2.0 | -<br>4.01g |
| HFCS | Fructose 55%, glucose 40% | 0 | 0 | 22 | C : 77.5<br>T : 80.3 | 64.5g<br>62.3g | -<br>3.3g | -<br>4.16g |
| Wheat flake cereal bricks | Wholegrain wheat, raw sugar, salt, barley malt extract, minerals (zinc gluconate, iron) vitamins (niacin, thiamin, riboflavin, folate) | 12 | 1.5 | 8 | C : 67<br>T1 : 67.1<br>T2 : 66.7 | 74.6g<br>74.5g<br>74.9g | -<br>1.4g<br>2.0g | -<br>2.08g<br>2.98g |

C = control product, T = test sample containing filtered molasses concentrate, ND = not determined. CHO = carbohydrate, HFCS = High Fructose Corn Syrup

| Food tested | GI ± SEM | % GI reduction | II ± SEM | % II reduction |
|---|---|---|---|---|
| White bread | C: 74 ± 3 | - | C: 78 ± 3 | - |
| | T: 59 ± 6 | 20% | T: 67 ± 6 | 14% |
| Glucose syrup | C: 107 ± 7 | - | C: 104 ± 4 | - |
| | T: 93 ± 9 | 13% | T: 87 ± 7 | 17% |
| Fruit flavoured beverage | C: 67 ± 5 | - | C: 66 ± 4 | - |
| | T: 58 ± 3 | 13% | T: 56 ± 3 | 13% |
| Energy bar | C: 45 ± 6 | - | C: 61 ± 3 | - |
| | T: 40 ± 4 | 11% | T: 63 ± 3 | - 3.3% |
| HFCS | C: 56 ± 5 | - | C: 65 ± 5 | - |
| | T: 50 ± 3 | 11% | T: 58 ± 3 | 11% |
| Wheat flake cereal bricks | C: 76 ± 5 | - | ND | |
| | T1: 72 ± 5 | 5% | ND | ND |
| | T2: 70 ± 4 | 8% | ND | ND |

C = control product, T = test sample containing filtered molasses concentrate, SEM = Standard error of the mean, ND = not determined.

Figure 3

A
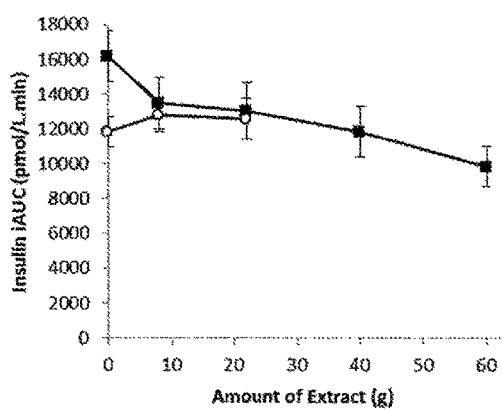
B
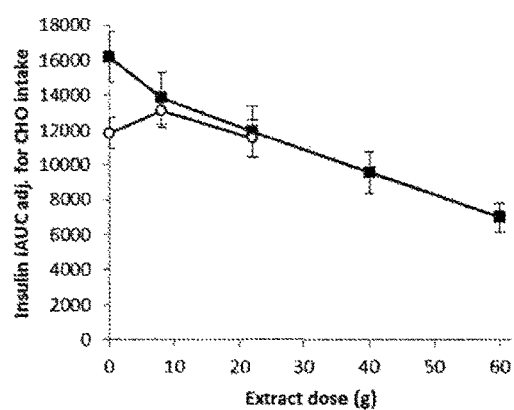
Figure 11

SUGAR CANE DERIVED EXTRACTS AND METHODS OF TREATMENT

FIELD OF THE INVENTION

The invention relates to extracts produced from sugar cane and sugar beet waste and other processing stream products having desirable properties and health benefits. More particularly the invention relates to extracts obtained from molasses, methods of producing the extracts, and uses of the extracts for management of insulin resistant conditions.

BACKGROUND OF THE INVENTION

Sugar is a common carbohydrate sourced from sugar cane and sugar beet used in food because of its sweet taste. Approximately 70% of the world's sugar comes from sugar cane and about 30% comes from beets. Ordinary table sugar (sucrose) is a disaccharide made up of one molecule of glucose bound by a α-I,2-glycosidic linkage to one molecule of fructose.

The processing of sugar cane (see FIG. 12), results in the generation of a number of byproducts, most of which are considered waste products with little or no nutritional value or use in human applications. Typically they are difficult to refine further and there are often substances in the compositions that contaminate standard separating materials. However, molasses and other products of the sugar refining process, are complex mixtures of compounds, including organic molecules such as polyphenols, di/tri/polysaccharides, peptides/proteins, minerals, and organic acids.

Polyphenols (compounds with two or more phenol groups) and phenolic acids (one phenol ring—also called phenolics) are a class of phytochemicals found in a variety of sources including wine, grapes, cocoa and sugar cane and sugar beet. Polyphenols and phenolics all have a common basic chemical component, that is, a phenolic ring structure. There are at least 8000 identified polyphenols in a number of subcategories, such as anthocyanidins and catechins. Natural polyphenols can range from simple molecules such as phenolic acid to large highly polymerized compounds such as tannins. Polyphenols can exist in their free form, or as polyphenol glycosides.

Conjugated forms of polyphenols are the most common, where various sugar molecules, organic acids and lipids (fats) are linked with the phenolic ring structure. Despite having a common phenolic ring structure, differences in the conjugated chemical structure, size and other substituents account for different chemical classifications and significantly, variation in the potential biological activity, modes of action and potential influence on metabolism and resulting influence on human (or animal) health properties of the various compounds.

Role of Polyphenols in Blood Glucose Control

Polyphenols from different plant sources have been associated with a plethora of health benefits including in respect of their positive effect on the rate of carbohydrate digestibility in the body and in turn, the effect on blood glucose levels. It is on this basis that polyphenols have been used to lower the glycemic index (GI) of foods (see for example WO2005/117608 to the applicants).

The GI of a food is a measure of how quickly blood sugar levels (i.e., levels of glucose in the blood) rise after eating a particular type of food. Foods are grouped by GI value into categories: High GI>70; Medium GI between 69 and 56; and Low GI<55 (Foster Powell and others 2002; Atkinson and others 2008), whereby the lower the GI value, the slower blood sugar levels rise after having eaten the food. The GI of a food product is dependent on a range of factors, many of which are intrinsic to the food and include the levels of polyphenols. When added to foods, for example, polyphenols from green tea and soluble fibre from barley β-glucan were found to be effective in reducing the fasting plasma glucose levels of induced diabetic rats (Gao and others 2012).

The GI of foods however has been criticized for ignoring the relevance of the postprandial insulin response and the role of hyperinsulinaemia in the development of diabetes and metabolic syndrome. Continuously high insulin levels is a more significant determinant of the development of insulin-resistant conditions such as diabetes.

Physiologically, once glucose is sensed in the blood after digestion of the food and subsequent absorption from the intestine, the body (via incretins) activates the production and secretion of insulin which sends signals to the body to activate glucose uptake receptors in muscle, liver and other tissues to absorb the glucose from the blood, since glucose is the basic energy form used by the different cells and tissues in the body. Continuously high levels of glucose in the blood leads to the development of insulin-resistance, also referred to as impaired-glucose tolerance. Under such conditions, the body is unable to properly clear glucose in spite of high levels of insulin. This represents the first stage in the development of diabetes (pre-diabetes) and over time if this is not corrected, the pancreas (the organ which produces insulin) becomes overworked and unable to produce insulin. By that time, type 2 diabetes has developed.

The Insulin Index (II) is a measure used to quantify the typical insulin response to various foods. It is a measure of the insulin response in the blood over two hours after ingestion of a test food. It is often done in conjunction with GI. This measure provides additional information to the GI as some foods can still cause an insulin response despite there being no carbohydrates present. Thus, the insulinaemic index (II) (also referred to as the Insulin Index) can be used as an additional metric for classifying foods (Lee and Wolever 1998).

Not only do existing products on the market fail to consider the relevance and regulation of the insulin response, but they fail to ensure the very careful balance required to ensure that at the other end of the scale, the subject does not become hypoglycaemic. That is, glucose levels being too low. This is an important requirement for developing useful compositions for the management of conditions associated with insulin resistance, and in particular, obesity and type 2 diabetes. It is for at least this reason that the European Food Safety Authority (EFSA) requires that reductions in postprandial glucose responses to foods are not the result of an increase in insulin response, which would place undue stress on the pancreatic cells producing insulin. For example adding extra protein will cause higher insulin secretion and subsequent lower blood glucose levels.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

The invention relates to extracts obtained from waste products or other products of sugar cane processing streams, i.e. sugar cane derived extracts, particularly molasses, optionally in combination with other compounds to create compositions and food products that are capable of lowering the Glycaemic Index (GI) of a substance, product or food, and preferentially lowering the postprandial glucose and insulin responses to that substance or product, or a meal, without leading to hypoglycaemia (low blood sugar). This effect is relevant in improving insulin sensitivity which has implications in the management of conditions associated with insulin resistance. In particular, the management of type 2 diabetes and obesity.

The invention seeks to manage the balance between the glucose response and the insulin response. That is, sufficient insulin in the blood to manage glucose levels, but not so much insulin that the glucose is absorbed from the blood stream too quickly and the subject becomes hypoglycaemic. In other words, upon administration of the sugar cane derived extracts of the invention the insulin response is lowered to a greater extent than the glucose level, so the ratio of insulin to glucose levels is reduced.

The waste products or other products of sugar cane processing streams are herein referred to more simply as "sugar cane derived products". The extracts of the invention, obtained from sugar cane derived products are herein referred to as "sugar cane derived extracts".

The sugar cane derived extracts of the invention are unique in that unlike any other extract or polyphenol product on the market, they do not inhibit glycolytic enzymes. The effect of inhibiting these enzymes is a reduction in the amount of glucose entering the blood, thus limiting the insulin response. However, one of the limitations of glycolytic enzyme inhibitors is that they can also lead to hypoglycaemia, which is also undesirable, given glucose is the major energy source for the body's cells.

In one aspect of the invention there is provided a method for treating conditions in a subject associated with insulin resistance comprising the administration of a sugar cane derived extract enriched in polyphenols (as herein defined), wherein the administration of the sugar cane derived extracts lowers postprandial glucose and insulin responses without leading to hypoglycaemia.

In another aspect of the invention there is provided a method of lowering postprandial glucose and insulin responses without leading to hypoglycaemia in a subject with a condition associated with insulin resistance, comprising the administration of a sugar cane derived extract enriched in polyphenols (as herein defined), thereby treating the condition.

Preferably the condition associated with insulin resistance is type 2 diabetes.

The sugar cane derived extracts of the invention enriched in polyphenols are preferably extracted from the sugar cane derived product molasses. A sugar cane derived extract of the invention may be selected from one or more of.

A sugar cane derived extract produced from mechanical filtration of mill molasses using a 30-35 kDa cut off membrane, containing 1-1.5 g of polyphenols/100 g in a liquid (i.e. syrup) form;

A sugar cane derived extract further processed after passing through a 30-35 kDa filter by ion exclusion chromatography (such as with a sulfonic acid resin) containing 4-8 g polyphenols/100 g in a liquid (i.e. syrup) form; or, alternatively, 6.5-13.5 g polyphenols/100 g when dried to a powder;

A sugar cane derived extract, comprising, the retained compounds of molasses subjected to hydrophobic chromatography, containing 20-30 g polyphenols/100 g when dried to a powder.

Each of these is initially produced as a syrup but may be dried to a powder. Total polyphenol content is expressed as catechin equivalents (CE). The 1-1.5 of polyphenols/100 g referred to above, for example, is written as 1-1.5 g CE/100 g.

A sugar cane derived extract produced from mechanical filtration of mill molasses using a 30-35 kDa cut off membrane containing 1-2 g of polyphenols/100 g typically contains the following in a syrup:

| Component | |
|---|---|
| Polyphenols g CE/100 g | 1-1.5 g |
| Moisture, g/100 g | 30-45 |
| Energy, (calc) kJ/100 g | 800-1000 |
| Protein (N × 6.25, g/100 g) | 1-3 |
| Fat, g/100 g | 0.5-1.2 |
| Sucrose, g/100 g | 20-40 |
| Glucose, g/100 g | 3-10 |
| Fructose, g/100 g | 5-10 |
| Total sugars, g/100 g | 28-60 |
| Sodium, mg/100 g | 45-55 |
| Soluble dietary fibre, g/100 g | 0-1 |
| Ash, g/100 g | 5-10 |
| Total carbohydrate (by difference, g/100 g) | 45-60 |
| Calcium, mg/kg | 5000-6000 |
| Iron, mg/kg | 70-100 |
| Magnesium, mg/kg | 1700-2500 |
| Potassium, g/kg | 20-40 |

A sugar cane derived extract further processed after passing through a 30-35 kDa filter by ion exclusion chromatography (such as with a sulfonic acid resin) containing 4-8 g polyphenols/100 g or, alternatively, 85-135 g polyphenols/kg dry weight, typically contains the following:

| Component | |
|---|---|
| Polyphenols (g CE/100 g) | 4-8 |
| Moisture, g/100 g | 30-50 |
| Energy, (calc) kJ/100 g | 720-1030 |
| Protein (N × 6.25, g/100 g) | 0-3 |
| Fat, g/100 g | 0-0.5 |
| Sucrose, g/100 g | 10-20 |
| Glucose, g/100 g | 15-25 |
| Fructose, g/100 g | 15-25 |
| Total sugars, g/100 g | 40-70 |
| Sodium, mg/100 g | 1-10 |
| Soluble dietary fibre, g/100g | 0-1 |
| Ash, g/100 g | 5-10 |
| Total carbohydrate (by difference, g/100 g) | 45-60 |
| Calcium, mg/kg | 500-600 |
| Iron, mg/kg | 7-10 |
| Magnesium, mg/kg | 170-250 |
| Potassium g/kg | 2-4 |

A sugar cane derived extract, comprising the retained compounds of molasses subjected to hydrophobic chromatography, containing 20-30 g polyphenols/100 g, typically contains the following:

| Component | |
|---|---|
| Polyphenols (g CE/100 g) | 20-30 |
| Moisture, g/100 g | 3-8 |
| Energy, (calc) kJ/100 g | 1500-2500 |
| Protein (N × 6.25, g/100 g) | 10-15 |

-continued

| Component | |
|---|---|
| Fat, g/100 g | 0-0.2 |
| Sucrose, g/100 g | 0-0.2 |
| Glucose, g/100 g | 0-0.2 |
| Fructose, g/100 g | 0-0.2 |
| Total sugars, g/100 g | 0-1 |
| Sodium, mg/100 g | 1-10 |
| Soluble dietary fibre, g/100 g | 0-1 |
| Ash, g/100 g | 0-5 |
| Total carbohydrate (by difference, g/100 g) | 70-90 |
| Calcium, mg/kg | 7000-9500 |
| Iron, mg/kg | 1200-1600 |
| Magnesium, mg/kg | 2200-2700 |
| Potassium, mg/kg | 250-350 |

In each of these embodiments, the regulation by lowering of the postprandial glucose and insulin response is done in such a way to protect against hypoglycaemia. In this regard, in one embodiment, it is beneficial if the sugar cane derived extracts administered comprise 20-40% total sugars.

The insulin response of a subject is dependent on the metabolic state (or status) of subjects. Accordingly, it is preferred to assess the metabolic state of the subject, and to do so before the sugar cane derived extracts of the invention are administered. Subjects with a predisposition to insulin resistance and the conditions that result or an existing condition associated with insulin resistance will benefit most from administration or consumption of the extracts of the invention. In one aspect of the invention there is provided a method for treating conditions in a subject associated with insulin resistance comprising the steps of:
a) diagnosing the subject as having a condition associated with insulin resistance; and
b) administering a sugar cane derived extract enriched in polyphenols (as herein defined),
wherein the administration of the sugar cane derived extracts lowers postprandial glucose and insulin responses without leading to hypoglycaemia.

In another aspect of the invention there is provided a method of lowering postprandial glucose and insulin responses in a subject with a condition associated with insulin resistance without leading to hypoglycaemia, comprising the steps of:
a) diagnosing the subject as having a condition associated with insulin resistance; and
b) administering a sugar cane derived extract enriched in polyphenols (as herein defined) to the subject, thereby treating the condition.

In an alternative embodiment, step (a) of these embodiments comprises diagnosing the subject as having a predisposition to a condition associated with insulin resistance. The subject may have one or more risk factors for (i.e. a predisposition to) insulin resistance selected from the group of being over the age of 30; having a body mass index (BMI) greater than 23; having fasting glucose levels above 5 mmol/L; and being more insulin resistance as defined by various validated equations (such as, for example, the Matsuda Index and HOMA-IR) based on relative blood glucose and insulin levels at various postprandial time points.

In one form of the methods of the invention above for lowering postprandial glucose, the subject has been diagnosed as having a condition associated with insulin resistance before they are administered the sugar cane derived extract, or one that has a predisposition to a condition associated with insulin resistance. In this form, the sugar cane derived extract is administered to subjects known to have such a condition or known to be predisposed to it.

In one aspect of the invention there is provided a sugar cane derived extract enriched in polyphenols (as herein defined) for use in treating a subject with a condition associated with insulin resistance or a subject predisposed to a condition associated with insulin resistance wherein administration of the sugar cane derived extract lowers postprandial glucose and insulin responses without leading to hypoglycaemia.

In another aspect of the invention there is provided a sugar cane derived extract enriched in polyphenols (as herein defined) for use in lowering postprandial glucose and insulin responses without leading to hypoglycaemia in a subject with a condition associated with insulin resistance, or a subject predisposed to a condition associated with insulin resistance.

In these uses of the invention, the sugar cane derived extract used is one of the same as described above, being
A sugar cane derived extract produced from mechanical filtration of mill molasses using a 30-35 kDa cut off membrane, containing 1-1.5 g of polyphenols/100 g in a liquid (i.e. syrup) form;
A sugar cane derived extract further processed after passing through a 30-35 kDa filter by ion exclusion chromatography (such as with a sulfonic acid resin) containing 4-8 g polyphenols/100 g in a liquid (i.e. syrup) form; or, alternatively, 6.5-13.5 g polyphenols/100 g when dried to a powder; or
A sugar cane derived extract, comprising the retained compounds of molasses subjected to hydrophobic chromatography, containing 20-30 g polyphenols/100 g when dried to a powder;
each having the components and amounts thereof as described in the tables above respectively.

It is also preferred that, in the above described uses of the sugar cane derived extract, the subject to whom the sugar cane derived extract is being administered, or who is consuming the sugar cane derived extract, is one that has been diagnosed as having a condition associated with insulin resistance before they receive the sugar cane derived extract, or one that has a predisposition to a condition associated with insulin resistance.

There is also provided use of a sugar cane derived extract enriched in polyphenols (as herein defined) in the preparation of a medicament for treating a subject with a condition associated with insulin resistance or a subject predisposed to a condition associated with insulin resistance, wherein administration of the medicament lowers postprandial glucose and insulin responses without leading to hypoglycaemia.

In an alternative embodiment, there is provided use of a sugar cane derived extract enriched in polyphenols (as herein defined) in the preparation of a medicament for lowering postprandial glucose and insulin responses without leading to hypoglycaemia in a subject with a condition associated with insulin resistance, or a subject predisposed to a condition associated with insulin resistance.

The sugar cane derived extract used in the preparation of a medicament is again the same as described in the methods and uses above, and in a preferred embodiment, the subjects have first been diagnosed as having a condition associated with insulin resistance before they receive the sugar cane derived extract, or one that has a predisposition to a condition associated with insulin resistance.

In each of the methods and uses of the invention, the sugar cane derived extract or the medicament may be a dietary supplement, food ingredient or a medical food. For this reason, it is to be understood that 'administration' is intended to encompass consumption.

In each of these embodiments, the condition associated with insulin resistance is type 2 diabetes.

In each of the methods and uses of the invention the sugar cane derived extract is administered in an amount that is sufficient to lower postprandial glucose, and to lower the insulin response, and in doing so, for hypoglycaemia to be avoided. The extract and method have a broader therapeutic window. This is because unlike known products for lowering postprandial glucose, an excessive amount will not lead to hypoglycaemia, thus avoiding the need to remain below a toxic upper limit of the amount of extract that can be administered, while protecting against hypoglycaemia.

BRIEF DESCRIPTION OF THE DRAWINGS

FIG. 2 summarises the composition and nutrition information for a sugar cane derived extract of the invention from molasses (referred to in the figures and examples as 'molasses extract') in comparison to mill molasses. Molasses extract retains approximately 70-75% of most components. Although viscosity of mill molasses has not been tested, molasses extract is visibly less viscous than mill molasses due to removal of colloids, fibre and other high molecular weight compounds. (CE=catechin equivalents, db=dry basis).

FIG. 3 summarises the foods tested for GI, II (FIG. 3A) and the reduction of glucose and insulin responses (FIG. 3B): Addition of molasses extract syrup reduces glycaemic index (GI) in each food matrix tested. Degree of GI reduction is dependent on ratio of extract to available carbohydrate (see FIG. 4). At the same time, insulin index (II) is reduced in all food matrices except the energy bar, which also contains protein and fat. Insulin index reductions are not related directly to molasses extract content either by weight or relative to carbohydrate content. C=control product, T=test sample containing molasses extract syrup, ND=not determined

FIG. 11. Insulin responses to molasses extract. Insulin incremental area under the curve (iAUC) responses are compared between "at-risk" subjects included in the extended study (n=15, closed squares) and those not included (n=23, open circles). (A) Insulin iAUC (mean±SEM) plotted against amount of molasses extract ingested. (B) Insulin iAUC standardised by the amount of available carbohydrate in each meal/dose combination (arbitrarily adjusted to 64.8 g, the amount of carbohydrate in the placebo test; mean±SEM) and then plotted against the amount of molasses extract ingested. Adj., adjusted; CHO, carbohydrate.

DETAILED DESCRIPTION OF THE EMBODIMENTS

Figure 1:
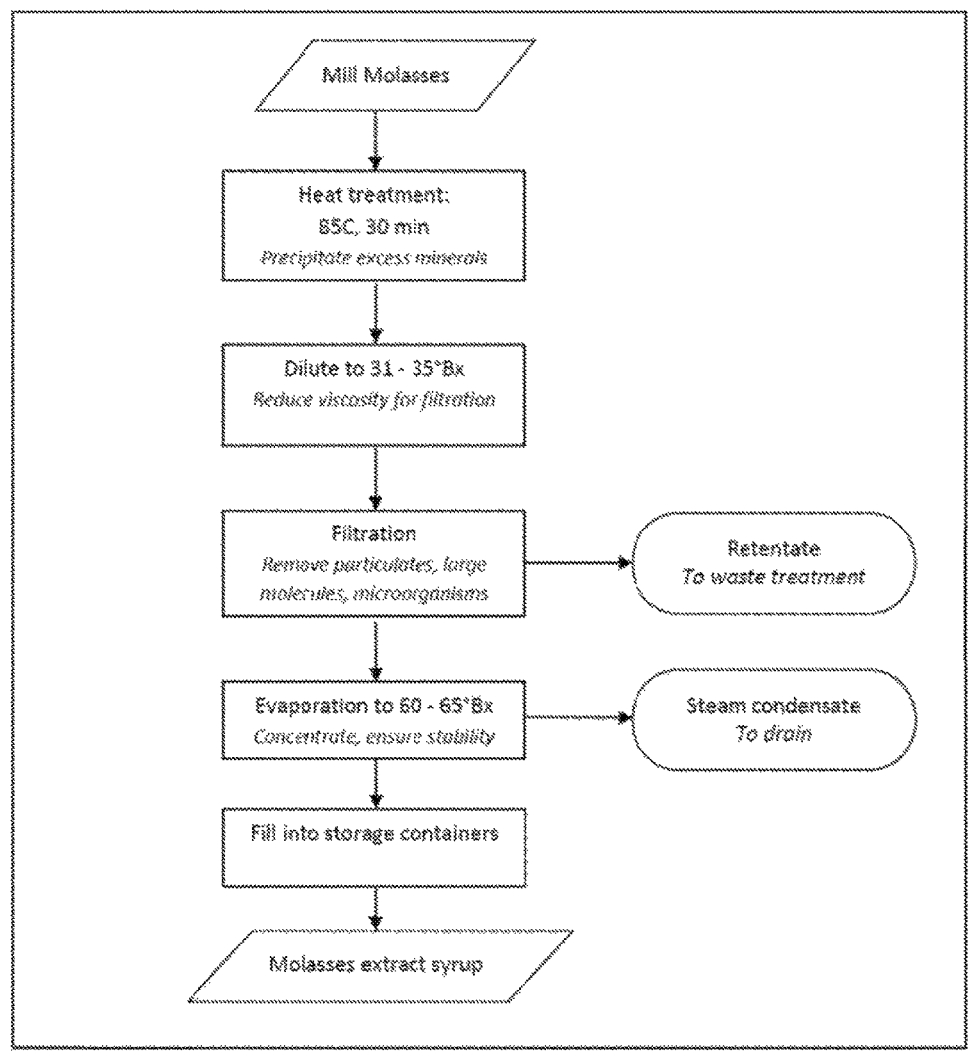
FIG. 1 is a flow chart of one of the sugar cane molasses extraction processes

The invention relates to extracts obtained from sugar cane waste and other processing streams and the use of the extracts of the invention in substances and products such as foods, wherein the substance or product can be administered to a subject in order to regulate postprandial glucose and insulin responses without leading to the subject becoming hypoglycaemic (low blood sugar). Regulating postprandial glucose and insulin responses in the context of this invention is the lowering of those responses such that glucose enters the blood stream at a slower rate, and that the insulin response does not clear glucose from the subject so quickly that they become hypoglycaemic (i.e. low glucose levels). The invention therefore seeks to manage the balance between the glucose response and the insulin response. That is, sufficient insulin in the blood to manage glucose levels, but not so much insulin that the glucose is cleared too quickly and the subject becomes hypoglycaemic. In other words, upon administration of the sugar cane derived extracts of the invention the insulin response is lowered to a greater extent than the glucose level, so the ratio of insulin to glucose levels is reduced.

The subjects are those having, or having a predisposition to, conditions associated with insulin resistance. In particular, the condition is type 2 diabetes.

A study by Lan-Pidhainy and Wolever 2011 demonstrated that the GI of foods was independent of metabolic status of the subjects. That is, after consumption of the same food, a person's blood sugar rose at the same rate, regardless of whether they were healthy, hyperinsulinaemic or diabetic subjects. In contrast, there was variation in the insulin response among the different subjects suggesting that insulin response is dependent on the metabolic state of subjects. Holt et al. (1997) summarise studies that have shown that prolonged or high degrees of postprandial insulinaemia are thought to contribute to the development of insulin resistance and associated diseases such as obesity and type 2 diabetes. It is for at least this reason, as noted earlier, that the European Food Safety Authority (EFSA) requires that reductions in postprandial glucose responses to foods are not the result of an increase in insulin response. For example adding extra protein will cause higher insulin secretion and subsequent lower blood glucose levels.

The sugar cane derived extracts are prepared in a way that ensures they retain and concentrate the beneficial polyphenols present naturally in sugar cane. The polyphenols include, but are not limited to ferulic acid, orientin, cyanidin-3-O-glucoside, p-coumaric acid, malvidin-glycoside, epigallocatechin and diosmin. The sugar cane derived extracts of the invention have those polyphenols present in higher concentrations than they occur in the sugar cane derived products from which they are extracted. That is, there is a higher relative abundance of those polyphenols in the sugar cane derived extract compared to the starting material. Depending on the method of making the sugar cane derived extract, this can mean that there is a higher relative abundance of smaller molecular weight polyphenols, preferably those less than 30 kDa, or a higher relative abundance of hydrophobic polyphenols, compared to molasses itself. This is what is meant by the term as used herein "enriched in polyphenols".

As noted above, sugar cane derived products are the sugar cane waste and other products of processing streams. In the case of a molasses extract, the sugar cane derived product is molasses, and the molasses extract enriched in polyphenols has a higher relative concentration of polyphenols than molasses that has not been subjected to a process for preparing an extract. The reason being that in the process of making an extract of the invention, components are removed, meaning the remaining polyphenols now represent a higher proportion of the total mixture. In absolute terms, molasses may have higher overall levels of polyphenols. However the extraction process may remove the very high molecular weight polyphenols, like tannins and melanoidins, or the more hydrophilic polyphenols leaving behind an enriched, higher relative proportion of the remaining polyphenols.

Molasses itself however is not an extract from sugar cane, as extract is used in the context of this invention. The sugar cane derived extracts of the invention have been subjected to additional treatment steps other than those that occur as part of the natural sugar cane processing scheme.

By polyphenols, as used herein, it is meant polyphenols in their free form, polyphenols as polyphenol glycosides, conjugated forms of polyphenols, and phenolic acids. The term polyphenols, as used throughout the specification, collectively refers to all of these forms of polyphenols.

The sugar cane derived extracts of the invention are the first to be described that have been recognised as protecting against hypoglycaemia. They lower the glucose response, and in most subjects (especially those already predisposed to insulin resistance) it is anticipated that the insulin response is preferentially lowered to a more significant extent than glucose such that the insulin doesn't clear the glucose too quickly and render the subject hypoglycaemic. In other words, the extracts:
- lower the glucose response and therefore the GI of a substance after consumption or administration of the substance (i.e. regulating blood glucose responses); and preferably
- lower the insulin response (i.e. regulating insulin response) of the body to that substance; and
- lower the risk of hypoglycaemia.

Insulin resistance is a physiological condition in which cells fail to respond to the normal actions of the hormone insulin. The pancreas produces insulin, but the cells in the body become resistant to insulin. This often remains undetected and can lead to type 2 diabetes (also called non-insulin dependent diabetes), metabolic syndrome and obesity. An important aspect of treating conditions associated with insulin resistance is to regulate the postprandial glucose and insulin responses in the subject, while ensuring that the subject does not become hypoglycaemic either. By 'hypoglycaemic' it is meant low blood glucose. The level of blood glucose low enough to define hypoglycaemia may vary from person to person. But most healthy adults maintain fasting glucose levels above 4.0 mmol/L (72 mg/dl), and develop symptoms of hypoglycaemia when the glucose falls below 4 mmol/L.

In some subjects, and some conditions, insulin levels are higher than that required for removal of postprandial glucose, or they continue to be elevated after all glucose has been taken up by the tissues, resulting in reactive hypoglycaemia. The risk to insulin resistant subjects is similar. Continuing high insulin levels after postprandial glucose has been removed from the blood causes hypoglycaemia. As noted above, upon administration of the sugar cane derived extracts of the invention the insulin response is lowered to a greater extent than the glucose level, so the ratio of insulin to glucose levels is reduced.

In one aspect of the invention there is provided a method for treating a subject having a condition associated with insulin resistance, or for treating a subject predisposed to a condition associated with insulin resistance, comprising administering to the subject a sugar cane derived extract enriched in polyphenols (as herein defined), wherein the administration of the sugar cane derived extract lowers postprandial glucose and insulin responses without leading to hypoglycaemia. As defined above, enriched in polyphenols means that extract has polyphenols present in higher concentrations than they occur in the sugar cane derived product from which they are extracted.

The sugar cane derived extract is preferably administered in the form of a dietary supplement, medical food or food ingredient. Accordingly, 'administered' would also be understood to include consumption of the extract.

The regulation occurs in the context of postprandial regulation. That is, after consumption of food. By 'regulating postprandial glucose and insulin responses' it is meant that after a meal for example, and administration of the extract as either part of that meal or as a supplement to that meal, both the glucose and insulin response is lowered compared to the levels at which that would occur in the absence of the extract. As noted above, the extract of the invention has glycaemic index (GI) lowering properties. The administration of the sugar cane derived extract of the invention in the ways referred to above therefore lowers the GI of the substance or food, meaning the rate of glucose entering the blood stream is lower and/or the rate of tissue uptake of glucose is increased. Lowering the GI of a substance therefore lowers and subsequently regulates the subject's postprandial glucose response in accordance with the invention.

Along the same lines, 'regulating the insulin response', in accordance with the invention, means lowering the insulin response. Despite the close physiological relationship between glucose and insulin responses, some foods can still cause an insulin response despite there being no sugars/carbohydrates present. This highlights the value of the extracts of the invention in being able to regulate both, and makes the extracts of the invention a very important component of compositions to regulate a subject's insulin response, especially in the context of subjects with an insulin resistant condition such as type 2 diabetes.

Accordingly, when the sugar cane derived extract is administered, it is administered in an amount that is sufficient to lower postprandial glucose, and to lower the insulin response, and in doing so, for hypoglycaemia to be avoided. There is no upper limit to the amount of extract that can be administered as the extract protects against hypoglycaemia. This is advantageous, as other products on the market that function to inhibit glycolytic enzyme can also lead to hypoglycaemia, which is also undesirable, given glucose is the major energy source for the body's cells.

As used herein, except where the context requires otherwise, the term "comprise" and variations of the term, such as "comprising", "comprises" and "comprised", are not intended to exclude further additives, components, integers or steps.

In another aspect of the invention there is provided a method of lowering postprandial glucose and insulin responses without leading to hypoglycaemia in a subject with a condition associated with insulin resistance, or in a subject predisposed to a condition associated with insulin resistance, comprising the administration of a sugar cane derived extract enriched in polyphenols, (as herein defined) thereby treating the condition.

As the insulin response of a subject is dependent on the metabolic state of subject, it is preferred to assess the metabolic state of the subject prior to the administration of the extract of the invention. The methods of the invention may therefore further comprise a step (a) of diagnosing the subject as having a condition associated with insulin resistance, prior to step (b) of administering a sugar cane derived extract enriched in polyphenols.

The sugar cane derived extract of the invention is also able to reduce the risk of a subject predisposed to insulin resistance to developing conditions associated with insulin resistance, such as type 2 diabetes and obesity. Subjects at risk of developing insulin resistance and subsequent type 2 diabetes are, for example, those over the age of 30, those with a body mass index (BMI) greater than 23, those with fasting glucose levels above 5 mmol/L and those with elevated insulin resistance as defined by various validated equations (such as, for example, the Matsuda Index and HOMA-IR) based on relative blood glucose and insulin levels at various postprandial time points. The methods of the invention may therefore further comprise a step of determining a subject's predisposition to insulin resistance by screening for any one or more of these parameters.

In one form of the methods of the invention above for lowering postprandial glucose, the subject has been diagnosed as having a condition associated with insulin resistance before they are administered the sugar cane derived extract, or one that has a predisposition to a condition associated with insulin resistance. In this form, the sugar cane derived extract is administered to subjects known to have such a condition or known to be predisposed to it.

'Treat', 'treating' and 'treatment' are all used herein to mean slow down (lessen) an undesired physiological change or disorder. For purposes of this invention, beneficial or desired results include, but are not limited to, alleviation of symptoms of insulin resistant conditions, stabilised (i.e., not worsening or progressing) insulin resistant conditions, and inhibition of progression to an insulin resistant condition in subjects who are predisposed to the development of such conditions. The extract of the invention, by virtue of its role in regulating postprandial glucose and insulin responses without leading to hypoglycaemia is therefore able to (i) treat the particular disease, condition, or disorder, (ii) attenuate, ameliorate, or eliminate one or more symptoms of the particular disease, condition, or disorder, (iii) prevent or delay the onset of one or more symptoms of the particular disease, condition, or disorder described herein, (iv) prevent or delay progression of the particular disease, condition or disorder, or (v) reverses damage caused prior to treatment to some extent. The reversal does not have to absolute. Weight loss in a type 2 diabetes subject, or an obese subject, is an example of reversal of damage.

The sugar cane derived extract enriched in polyphenols (as herein defined) are also for use in treating a subject with a condition associated with insulin resistance or a subject predisposed to a condition associated with insulin resistance wherein administration of the sugar cane derived extract lowers postprandial glucose and insulin responses without leading to hypoglycaemia.

In another aspect of the invention the sugar cane derived extract enriched in polyphenols (as herein defined) is for use in lowering postprandial glucose and insulin responses without leading to hypoglycaemia in a subject with a condition associated with insulin resistance, or a subject predisposed to a condition associated with insulin resistance.

In these uses of the invention, the sugar cane derived extract used is the same as described above, and preferably from molasses.

It is also preferred that in the above described uses of the sugar cane derived extract, the subject to whom the sugar cane derived extract is being administered, or who is consuming the sugar cane derived extract, is one that has been diagnosed as having a condition associated with insulin resistance before they receive the sugar cane derived extract, or one that has a predisposition to a condition associated with insulin resistance.

There is also provided use of a sugar cane derived extract enriched in polyphenols (as herein defined) in the preparation of a medicament for treating a subject with a condition associated with insulin resistance or a subject predisposed to a condition associated with insulin resistance, wherein administration of the medicament lowers postprandial glucose and insulin responses without leading to hypoglycaemia.

In an alternative embodiment, there is provided use of a sugar cane derived extract enriched in polyphenols (as herein defined) in the preparation of a medicament for lowering postprandial glucose and insulin responses without leading to hypoglycaemia in a subject with a condition associated with insulin resistance, or a subject predisposed to a condition associated with insulin resistance.

The sugar cane derived extract used in the preparation of a medicament is again the same as described in the methods and uses above, and in a preferred embodiment, the subjects have first been diagnosed as having a condition associated with insulin resistance before they receive the sugar cane derived extract, or one that has a predisposition to a condition associated with insulin resistance.

In each of the methods and uses of the invention, the sugar cane derived extract or the medicament may be a dietary supplement, food ingredient or a medical food. For this reason, it is to be understood that 'administration' is intended to encompass consumption.

In each of these embodiments, the condition associated with insulin resistance is preferably type 2 diabetes.

The extracts of the invention that can be used in the methods of the invention, or according to the uses of the invention, can be derived from any product derived from sugar cane including the sugar cane milling process, the sugar cane refining process to make sugar, and other processes using sugar cane products such as the manufacture of ethanol from molasses as part of the manufacture of rum. The sugar cane derived extract can be derived from the raw materials, in-process products, by-products, final products and waste streams. For example, the sugar cane derived product may be: the feed stream of raw sugar cane juice, clarified juice and concentrated juice syrup, treacle, molasses (obtained from a primary mill or refinery), golden syrup, brown sugar, bagasse, dunder, field trash, growing tips, pulp, cane strippings, pith and mill mud.

Preferably, the sugar cane derived extract is derived from bagasse or molasses; most preferably sugar cane molasses. As used herein, the term "molasses" refers to the dark syrup which is left behind after the raw sugar crystals are collected in the sugar mill, the viscous black syrup remaining after the sugar cane syrup (also called massecuite) has been centrifuged for the last time in the refinery or mill.

In one preferred embodiment, the polyphenols in the sugar cane derived include one or more of p-coumaric acid, ferulic acid, syringic acid, caffeic acid, chlorogenic acid, (−) epicatechin, apigenin, (+) catechin, quercetin, diosmin, rutin, shaftoside, tricin, hydroxyl propanone, orientin, cyanidin-3-O glucoside, luteolin, diosmetin, vitexin, malvidin-glycoside, petunidin rhamnoside, epigallocatechin and derivatives and mixtures thereof. Preferably, the polyphenols include at least ferulic acid, orientin, cyanidin-3-O-glucoside, p-coumaric acid, malvidin-glycoside, epigallocatechin and diosmin. These polyphenols are enriched in the sugar cane derived extracts relative to, for example, molasses. As already explained, this means that they are present in higher relative amounts or concentrations in the extract compared to the molasses, although molasses may still contain higher concentrations as a significant percentage of polyphenols in molasses consists of high molecular weight, non-bioavailable material such as melanoidins and Maillard reaction products.

The sugar cane derived extract of the invention may be added to other substances or ingredients to lower the GI of that substance. Due to the very unique properties of the sugar cane derived extracts of the invention, not only is the GI of that substance or ingredient lowered, but the insulin response in the subject to that substance or ingredient is reduced to a greater extent, and the risk of hypoglycaemia is lowered. By "lower the GI" and "GI lowering extract", it is meant that the GI of the substance to which the extract is added is lowered compared to the GI of the substance to which no extract has been added. It does not have to make the substance itself low GI (i.e. GI<55), although it may in fact do so depending on the substance.

In some embodiments, the sugar cane derived extract comprises some carbohydrates which improve its taste whilst maintaining its GI and II lowering characteristics. Typically, the sugar cane derived extract comprises carbohydrates such as monosaccharides and disaccharides. The extract may also contain xylan derived mono, di, tri and oligosaccharides, such as xylobiose, xylotriose and xylose. The sugar cane derived extract may include carbohydrates having GI increasing characteristics such as sucrose and glucose. However, the amount of any GI increasing carbohydrates in the sugar cane derived extract is not sufficient to detract significantly from the GI lowering characteristics of the sugar cane derived extract as a whole. In one embodiment of the invention it is preferred that the extract contains 20 to 40%, and preferably around 30% sucrose. An extract of the invention having this amount of sucrose still exhibits GI lowering characteristics, while at the same time, is able to lower the risk of the subject becoming hypoglycaemic.

The sugar cane derived extract of the invention comprises minerals including mineral complexes. Typically, the minerals are selected from magnesium, potassium, calcium and mixtures thereof. Other minerals which may be present include anions such as phosphate, sulphate and chloride.

In one embodiment of the invention, the sugar cane derived extract also comprises organic acids. Typically, the organic acids are selected from the group consisting of cis-aconitic acid, citric acid, phosphoric acid, gluconic acid, malic acid, trans-aconitic acid, succinic acid, lactic acid and mixtures thereof, and most preferably trans-aconitic acid.

The sugar cane derived extract of the invention is typically prepared as a syrup, but can be evaporated to provide a powder. The methods of the invention include consumption of the sugar cane derived extract in syrup form, powder form or in the form of a food, food ingredient or beverage to which the syrup or powder has been added. The powder may also be formulated as a capsule or tablet.

Typically the sugar cane derived extract of the present invention further comprises one or more additional optional components such as policosanols, phytosterols, lipids, phospholipids, protein, antioxidants, phytosterols such as 1-octacosanol, campesterol, stigmasterol, β-sitosterol, oligosaccharides such as raffinose, 1-kestose, theanderose, 6-kestose, panose, neo-kestose and nystose, aliphatic alcohols, vitamins, flavonoids (8 subgroups: Flavonols (e.g. quercetin, kaempferol, myricetin and isorhamnetin); Flavones (e.g. luteolin, tricin and apigenin); Flavanones (e.g. hesperetin, naringenin anderiodictyol); Flavan-3-ols (e.g. catechin, gallocatechin, epicatechin, epigallocatechin, epicatechin 3-gallate, epigallocatechin 3-gallate and theaflavin); Anthocyanidins (e.g. cyanidin, delphinidin, malvidin, pelargonidin, peonidin and petunidin); Anthocyanosides; Curcuminoids; and Proanthocyandins) and their derivatives, including but not limited to, natural and synthetic conjugates such as glycosides, glucosides, galactosides, galacturonides, ethers, esters, arabinosides, sulphates, phosphates, aldopentoses (xylose, arabinose) aldohexoses (mannose), ketopentoses, ketohexoses (fructose), kestoses, soluble gums, aliphatic alcohols (and complexes), waxes (and complexes), fibre, oligosaccharides, non-nitrogenous compounds, mineral complexes (organic iron and other minerals), phytochemical complexes (including but not limited to glucosides, glycosides, glycosylates, esters, glucopyranosides etc.), chlorophyll, phytosterols (and complexes), phytostanols (and complexes), hydrolysed celluloses and phospholipids. The term "policosanols", within the scope of the present invention, refers to the family of aliphatic alcohols and their derivatives, complexes or analogues which are found naturally in sugar cane. Examples include long chain fatty alcohols such as octacosanol, triacontanol, dotriacontanol, tetracosanol, hexacosanol, tetratriacontanol, hexatriacontanol and docosanol.

In one preferred embodiment, the sugar cane derived extract is a syrup derived from molasses and the extract has the following composition:

TABLE 1

| Component | Range | Preferred |
|---|---|---|
| Polyphenols, g CE/100 g | 1.0-1.5 | 1.15 |
| Moisture, g/100 g | 30-45 | 38.4 |
| Energy, (calc) kJ/100 g | 800-1000 | 946 |
| Protein (N × 6.25, g/100 g) | 1-3 | 2.0 |
| Fat, g/100 g | 0.5-1.2 | 0.9 |
| Sucrose, g/100 g | 20-40 | 29.3 |
| Glucose, g/100 g | 3-10 | 5.4 |
| Fructose, g/100 g | 5-10 | 6.0 |
| Total sugars, g/100 g | 28-60 | 40.7 |
| Sodium, mg/100 g | 45-55 | 50 |
| Soluble dietary fibre, g/100 g | 0-1 | 0.3 |
| Ash, g/100 g | 5-10 | 6.1 |
| Total carbohydrate (by difference, g/100 g) | 45-60 | 52.3 |
| Calcium, mg/kg | 5000-6000 | 5450 |
| Iron, mg/kg | 70-100 | 89 |
| Magnesium, mg/kg | 1700-2500 | 2000 |
| Potassium, g/kg | 20-40 | 24.5 |

As can be seen from Table 1, this is an embodiment of the invention that preferentially contains 20 to 40%, and preferably around 30% sucrose. This helps improve its taste whilst maintaining its GI and II lowering characteristics.

In an alternative embodiment, the extract is a syrup derived from molasses and the extract has the following composition:

TABLE 2

| Component | Range | Preferred |
|---|---|---|
| Polyphenols (g CE/100 g) | 4-8 | 6 |
| Moisture, g/100 g | 30-50 | 40 |
| Energy, (talc) kJ/100 g | 720-1080 | 900 |
| Protein (N × 6.25, g/100 g) | 0-3 | 0.5 |
| Fat, g/100 g | 0-0.5 | 0.1 |

TABLE 2-continued

| Component | Range | Preferred |
|---|---|---|
| Sucrose, g/100 g | 10-20 | 15 |
| Glucose, g/100 g | 15-25 | 20 |
| Fructose, g/100 g | 15-25 | 20 |
| Total sugars, g/100 g | 40-70 | 55 |
| Sodium, mg/100 g | 1-10 | 5 |
| Soluble dietary fibre, g/100 g | 0-1 | 0.1 |
| Ash, g/100 g | 5-10 | 6.1 |
| Total carbohydrate (by difference, g/100 g) | 45-60 | 52.3 |
| Calcium, mg/kg | 500-600 | 550 |
| Iron, mg/kg | 7-10 | 8 |
| Magnesium, mg/kg | 170-250 | 200 |
| Potassium | 2-4 | 2.45 |

In yet a further alternative embodiment, the extract is a powder derived from molasses and the extract has the following composition:

TABLE 3

| Component | Range | Preferred |
|---|---|---|
| Polyphenols (g CE/100 g) | 20-30 | 23 |
| Moisture, g/100 g | 3-8 | 5 |
| Energy, (calc) kJ/100 g | 1500-2500 | 1800 |
| Protein (N × 6.25, g/100 g) | 10-15 | 13 |
| Fat, g/100 g | 0-0.2 | 0.1 |
| Sucrose, g/100 g | 0-0.2 | 0.1 |
| Glucose, g/100 g | 0-0.2 | 0.1 |
| Fructose, g/100 g | 0-0.2 | 0.1 |
| Total sugars, g/100 g | 0-1 | 0.5 |
| Sodium, mg/100 g | 1-10 | 6 |
| Soluble dietary fibre, g/100 g | 0-1 | 0.1 |
| Ash, g/100 g | 0-5 | 3.4 |
| Total carbohydrate (by difference, g/100 g) | 70-90 | 79 |
| Calcium, mg/kg | 7000-9500 | 8800 |
| Iron, mg/kg | 1200-1600 | 1400 |
| Magnesium, mg/kg | 2200-2700 | 2400 |
| Potassium, mg/kg | 250-350 | 290 |

The above tables refer to preferred sugar cane derived extracts as they exit the manufacturing equipment. The sugar cane derived extracts may be further modified prior to their inclusion in commercial products. For example, the concentrations will change as the sugar cane derived extract is concentrated to form a syrup with a higher Brix, or if dried to form a powder. All such concentrated sugar cane derived extracts are included within the scope of this invention.

In another embodiment, the sugar cane derived extract may be a combination of sugar cane derived extracts from different sugar cane processing streams. For example, the desired phytochemical profile may be obtained by combining an extract of molasses with an extract of dunder. All such combined extracts are within the scope of this invention.

a) Method of Preparing the Sugar Cane Derived Extracts of the Present Invention

While there are methods in the art which subject sugar cane or sugar beet products to extraction and purification processes, the skilled person will appreciate that, depending on the purification/extraction/treatment process used, the composition of an end product will vary.

The physical characteristics of the sugar cane derived extracts of the present invention will depend on their overall chemical composition. Depending on the processing methods applied, the sugar cane derived extracts may be concentrated by evaporation, generating a syrup, or alternatively, the sugar cane derived extract could be fully dried to produce a powder. This ability to prepare sugar cane derived extracts having different physical properties increases the commercial utility of the sugar cane derived extracts.

Depending on their physical characteristics and chemical composition the sugar cane derived extracts will be suitable for various uses.

In a preferred embodiment, the sugar cane derived extract is produced using a method which comprises as one of its steps a fractionation by molecular weight and size, preferably by sequential micro- and ultra-filtration and optionally nano-filtration. This method is preferred where it is desirable to maintain a mixture of phytochemicals in the final sugar cane derived extract that more closely resembles that which exists in the sugar cane itself. One reason that this may be preferred is for taste. Prior art methods use separation processes which remove most of the carbohydrates, minerals and organic acids and the resultant extract is not representative of the natural balance that exists in the sugarcane. The extracts of the present invention are derived from sugar cane products, preferably molasses or bagasse from the cane sugar refining processes. The extract may be obtained from the sugar cane product by various methods, or combinations of methods. Preferably, the sugar cane derived extract is prepared by a filtration method, utilising microfiltration followed by ultrafiltration.

In one aspect of the present invention, the sugar cane derived extract is prepared by a method comprising the steps of:

(a) heating a solution of the sugar cane derived product (e.g. molasses, dunder, bagasse),
(b) precipitating salts from the solution,
(c) optionally diluting the solution of step (b)
(d) separating the precipitate from the solution by microfiltration, and
(e) fractioning the solution to isolate desired extracts.

One embodiment of this aspect of the invention involves:
(a) heating and diluting a sugar cane derived product such as molasses until the viscosity of the resulting solution is less than or equal to about 100 centipoise at a temperature in the range of from 40 to 60° C.;
(b) heating the product of step (a) to a temperature in the range of from 70 to 90° C. and then maintaining it in that temperature range for a period of time until a precipitate of insoluble calcium and magnesium salts forms;
(c) optionally diluting the solution of step (b) in order to reduce the viscosity of the solution to facilitate removal of the precipitate; dilution of the solution is to 30-65° Brix
(d) removing the precipitate and large particulate matter from the product of step (b) (or if diluted, the diluted product of step (c) by filtration;
(e) treating the product of step (d) with a fractionation by molecular weight and size to isolate desired extracts.

The product of step (e) can then be treated as required for storage. For example, the product may be concentrated via evaporation to 60 to 75° Brix.

Degrees Brix (°Brix or °Tx) is a term of art used to measure the sugar content of an aqueous solution. One degree Brix is 1 gram of sucrose in 100 grams of solution and represents the concentration of the solution as percentage by weight (% w/w).

Preferably, the temperature used in step (a) is about 50° C. Preferably, the viscosity achieved is in the range from 50 to 100 centipoise. Typically, water is used for the dilution in step (a). When the sugar cane derived product is molasses, a ratio of 1:2 to 2.5 volumes of molasses to water is typically used to provide the desired ratio. The preferred viscosity can also be adjusted by measuring the Brix, in which preferably the range is from 30 to 65° Brix, and more preferably from 35 to 45° Brix.

Preferably, the temperature in step (b) is about 85° C. Preferably, the period of time is in the range of from 20 to 40 minutes, more preferably about 30 minutes. Where necessary for the equipment used in step (d), the mixture from step (b) or (c) is cooled prior to step (d).

Step (d) can be achieved using any method known to a person skilled in the art for removing a precipitate. Typically it is carried out using a desludging centrifuge or other filtration methods including diatomaceous earth or fine muslin or similar material (i.e. microfiltration). For example, the mixture may be passed through a ceramic or stainless steel membrane (0.10 micron to 1.5 micron equivalent to 1000 kDa to 15000 kDa, preferably 0.1 to 0.5 micron equivalent to 1000 kDa to 5000 kD) using pressure e.g. about 4 Bar, a flow rate of 30 to 100 l/hour and at a temperature of 30 to 60° C., preferably 35 to 50° C. The retentate (typically the precipitate from step (d) and large particulate matter) is discarded (typically after washing with water having a pH in the range of from 7.2 to 7.5) and the permeate collected. In some applications, the retentate is not washed but is completely discarded. Alternatively, high speed continuous centrifugation could be used to remove the precipitate and large particulate matter.

Step (e) is undertaken using one or more fractionation filters or membranes selected from the group consisting of ultrafiltration, nanofiltration and mixtures thereof, to isolate desired extracts. The fractionation filters or membranes are known to persons skilled in the art of food processing. For example, the product from step (c) can be treated by passing it through a combination of spirally wound ultrafiltration (UF) membranes with size exclusion of:

an upper limit of about 100 kDa;
preferably an upper limit of about 50 kDa; and
more preferably an upper limit of about 30 kDa.

The term "about" in this context is used to indicate that the ranges are not intended to be limited to exactly 100 kDa for example. The skilled person would understand that this is intended to encompass sizes that are very close thereto.

Further fractionation can then be achieved with a 0.5 kDa nanofiltration membrane. A person skilled in the art will know that the choice of membrane used will depend on the desired final product, flow rate, pH, pressure, temperature and efficiency across a range of conditions. Typically, step (e) will occur at a temperature in the range of from 30 to 60° C., more typically 35 to 50° C.

The method described above is most useful for preparing a sugar cane derived extract described herein as being an extract produced from mechanical filtration of mill molasses using a 30-35 kDa cut off membrane, containing 1.0-1.5 g of polyphenols/100 g, and typically having the following composition in syrup form.

| Component | Range | Preferred |
|---|---|---|
| Polyphenols, g CE/100 g | 1.0-1.5 | 1.15 |
| Moisture, g/100 g | 30-45 | 38.4 |
| Energy, (calc) kJ/100 g | 800-1000 | 946 |
| Protein (N × 6.25, g/100 g) | 1-3 | 2.0 |
| Fat, g/100 g | 0.5-1.2 | 0.9 |
| Sucrose, g/100 g | 20-40 | 29.3 |
| Glucose, g/100 g | 3-10 | 5.4 |
| Fructose, g/100 g | 5-10 | 6.0 |
| Total sugars, g/100 g | 28-60 | 40.7 |
| Sodium, mg/100 g | 45-55 | 50 |
| Soluble dietary fibre, g/100 g | 0-1 | 0.3 |
| Ash, g/100 g | 5-10 | 6.1 |
| Total carbohydrate (by difference, g/100 g) | 45-60 | 52.3 |
| Calcium, mg/kg | 5000-6000 | 5450 |

-continued

| Component | Range | Preferred |
|---|---|---|
| Iron, mg/kg | 70-100 | 89 |
| Magnesium, mg/kg | 1700-2500 | 2000 |
| Potassium, g/kg | 20-40 | 24.5 |

In an alternative embodiment of this aspect of the invention, the product of step (e) is further de-calcified and the components separated by ion-exclusion chromatography with water as solvent. Steps (a) to (d) are essentially the same as described in the previous embodiment.

A person skilled in the art will know the choice of resin, flow rate, temperature and efficiency across a range of conditions. For example, the skilled person may elect to use a sulfonic acid resin with a flow rate of 0.5 B·V/h, at a temperature range from 30 to 80° C. The temperature can be varied depending on the viscosity of the product to be applied to the resin. Higher temperatures, around 80° C. are preferred for molasses derived extracts. Use of ion-exclusion chromatography in accordance with these exemplary conditions, and using molasses as a starting material, results in the production of 2 fractions. Broadly speaking, the majority of the salts, sucrose and larger undesired polyphenols are contained in the first fraction off the resin column as well as some of the monosaccharides glucose and fructose. The second fraction contains the majority of the monosaccharides glucose and fructose, and the rest of the desirable polyphenols. Further analysis by, for example, high performance liquid chromatography can optionally be done on the second fraction in order to analyse the compounds in the fraction or to validate the contents.

The method described above is most useful for preparing a sugar cane derived extract described herein as being an extract further processed after passing through a 30-35 kDa filter by ion exclusion chromatography (such as with a sulfonic acid resin) containing 4-8 g polyphenols/100 g or, alternatively, 65-135 g polyphenols/kg dry weight, and typically having the following composition in syrup form:

| Component | Range | Preferred |
|---|---|---|
| Polyphenols (g CE/100 g) | 4-8 | 6 |
| Moisture, g/100 g | 30-50 | 40 |
| Energy, (calc) kJ/100 g | 720-1030 | 900 |
| Protein (N × 6.25, g/100 g) | 0-3 | 0.5 |
| Fat, g/100 g | 0-0.5 | 0.1 |
| Sucrose, g/100 g | 10-20 | 15 |
| Glucose, g/100 g | 15-25 | 20 |
| Fructose, g/100 g | 15-25 | 20 |
| Total sugars, g/100 g | 40-70 | 55 |
| Sodium, mg/100 g | 1-10 | 5 |
| Soluble dietary fibre, g/100 g | 0-1 | 0.1 |
| Ash, g/100 g | 5-10 | 6.1 |
| Total carbohydrate (by difference, g/100 g) | 45-60 | 52.3 |
| Calcium, mg/kg | 500-600 | 550 |
| Iron, mg/kg | 7-10 | 8 |
| Magnesium, mg/kg | 170-250 | 200 |
| Potassium, g/kg | 2-4 | 2.45 |

Sugar cane derived extracts of the invention can also be produced by contacting molasses with a hydrophobic polymeric adsorbent to bind compounds including polyphenols in the molasses. This produces a sugar cane derived extract of the invention having a high relative abundance of hydrophobic compounds including polyphenols, and comprises the steps of:

a. contacting a sample of molasses with a hydrophobic polymeric adsorbent under conditions sufficient to enable binding of compounds to the adsorbent; and
b. eluting the bound compounds wherein the eluted product from step (b) has a high relative abundance of hydrophobic compounds including polyphenols compared to the sample of molasses i.e. prior to step (a).

A hydrophobic polymeric adsorbent suitable for use in these methods includes Amberlite XAD and Serdolit PAD. The skilled person would know of other brands.

More particularly, there is provided a method for producing a molasses extract of the invention with a high relative abundance of hydrophobic compounds including polyphenols comprising the steps of:

a. diluting the molasses to produce a 10 to 40% w/v aqueous solution;
b. optionally filtering the diluted molasses produced in step (a);
c. contacting the diluted molasses with a hydrophobic polymeric adsorbent under conditions sufficient to enable binding of compounds to the adsorbent and flow through of all other compounds in the diluted molasses;
d. optionally passing the flow through from step (c) over the hydrophobic polymeric adsorbent at least once;
e. optionally rinsing the hydrophobic polymeric adsorbent; and
f. eluting the compounds bound to the hydrophobic polymeric adsorbent to produce the extract wherein the compounds are eluted with 30 to 70% ethanol, preferably 40% ethanol, and optionally dried to form a powder.

The method described above is most useful for preparing an extract described herein as being a sugar cane derived extract, comprising the retained compounds of molasses subjected to hydrophobic chromatography, containing 20-30 g polyphenols/100 g, and typically having the following composition in powder form:

| Component | Range | Preferred |
|---|---|---|
| Polyphenols (g CE/100 g) | 20-30 | 23 |
| Moisture, g/100 g | 3-8 | 5 |
| Energy, (calc) kJ/100 g | 1500-2500 | 1800 |
| Protein (N × 6.25, g/100 g) | 10-15 | 13 |
| Fat, g/100 g | 0-0.2 | 0.1 |
| Sucrose, g/100 g | 0-0.2 | 0.1 |
| Glucose, g/100 g | 0-0.2 | 0.1 |
| Fructose, g/100 g | 0-0.2 | 0.1 |
| Total sugars, g/100 g | 0-1 | 0.5 |
| Sodium, mg/100 g | 1-10 | 6 |
| Soluble dietary fibre, g/100 g | 0-1 | 0.1 |
| Ash, g/100 g | 0-5 | 3.4 |
| Total carbohydrate (by difference, g/100 g) | 70-90 | 79 |
| Calcium, mg/kg | 7000-9500 | 8800 |
| Iron, mg/kg | 1200-1600 | 1400 |
| Magnesium, mg/kg | 2200-2700 | 2400 |
| Potassium, mg/kg | 250-350 | 290 | b) Use of Sugar Cane Derived Extract as a Dietary Supplement and Medical Food

Dietary supplements are nutritional additives that can be ingested without medical supervision and taken to augment daily dietary sources. Medical foods are specially formulated products given under medical supervision. These foods address a special nutritional requirement among patients with a specific disease that cannot be met by a normal diet or a diet with diet supplements.

As would be expected, administration of sugar cane derived extracts of the invention via dietary supplement or medical food typically involves oral consumption of the supplement or food. Oral consumption can be via eating or drinking a food or beverage, or taking a pill.

The sugar cane derived extracts of the present invention may be formulated as a dietary supplement optionally together with a pharmaceutically acceptable carrier, excipient or diluent. The dietary supplements comprising a sugar cane derived extract of the invention can be administered to or consumed by a subject to lower postprandial glucose and insulin responses without leading to hypoglycaemia, wherein the subject has a condition associated with insulin resistance, or is predisposed to having such a condition.

The sugar cane derived extracts of the present invention may also be incorporated into food products and beverages to create 'medical foods' that are to be used for lowering postprandial glucose and insulin responses without leading to hypoglycaemia in a subject with a condition associated with insulin resistance, or in a subject predisposed to having such a condition. The medical food comprising a sugar cane derived extract of the invention can be administered to or consumed by a subject to lower postprandial glucose and insulin responses without leading to hypoglycaemia, wherein the subject has a condition associated with insulin resistance, or is predisposed to having such a condition.

Preferably the sugar cane derived extracts are derived from molasses.

c) Use of the Sugar Cane Derived Extract as an Ingredient

The sugar cane derived extracts of the present invention may also be incorporated into food products and beverages for the purpose of increasing the overall health benefits of the food or beverage. In turn, when consumed as part of a normal diet, subjects will have beneficial effects from the sugar cane derived extracts of the invention on their postprandial glucose regulation and insulin response by the lowering of those responses.

Preferably the sugar cane derived extracts are derived from molasses.

The sugar cane derived extracts may be impregnated, mixed, emulsified, sprayed or coated onto carriers such as cellulose, methylcellulose, dextrose, cyclodextrose, cyclodextrin, maltitol, fibre and fibre containing bioactives to improve delivery. Delivery may also be enhanced with a range of surfactants, lipids, complexes, solvents and co-solvent pharmaceutical delivery systems known in the pharmaceutical art to improve bioavailability, absorption and efficacy.

As used herein, the term "food" or "food product" includes any edible product, such as but not limited to confectioneries, supplements, snacks (sweet and savoury), cocoa-containing foods, flavours and beverages, including foods, food products and beverages used in animal health and nutrition. Additional ingredients desired in the resulting food product may be added at any point in the process. In one embodiment of the invention, the sugar cane derived extract is in the form of a syrup that can be used as a substitute for regular glucose and high fructose corn syrups from wheat, corn, agave, *stevia* etc., as a functional ingredient to lower GI.

The sugar cane derived extracts of the present invention may be incorporated as functional ingredients into foods, beverages and nutraceuticals, including, without limitation, the following:

Dairy Products—such as processed cheeses, milk and other milk or dairy containing beverages, spreads and dairy mixes, ice cream and yoghurt;

Cereal-Based Products—comprising grains (for example, bread, cakes, muesli bars) whether these goods are cooked, baked or otherwise processed;

Confectioneries—such as chocolate, candies, chewing gum, desserts, non-dairy toppings or syrup condiments, sorbets, icings and other fillings, gelatin, starch based or pectin jellies;

Sports nutrition products including powders, pre-mixes juices, energy bars, isotonic drinks;

Beverages—whether hot or cold (coffee, tea, cocoa, cereal, chicory and other plant extract based beverages), alcoholic beverages, carbonated, non-carbonated and lightly carbonated beverages including colas and other soft drinks, powdered soft drinks, fruit and vegetable juice drinks, dietary supplement, breakfast beverages, instant pre-mixes and meal replacement drinks; sport drinks, energy drinks, flavoured water drinks;

Miscellaneous Products—including eggs and egg products, processed foods such as soups, pre-prepared pastas and pre-prepared pasta or curry sauces.

Similarly, food grade ingredients such as soluble fiber (e.g. oligofructosaccharide), insoluble fiber (e.g. sugar cane fiber, oat bran), flour, starch, modified starch, gelatin, or other food, pharmaceutical or cosmetic ingredients impregnated with or containing the sugar cane derived extract according to the invention, can produce a unique food ingredient with a lower GI and/or GI lowering capabilities.

The present invention includes food products comprising a sugar cane derived extract according to the invention alone as the active ingredient or in combination with other active ingredients.

The sugar cane derived extract of the invention may be added to other substances, products or ingredients to lower the GI of the substance, product or ingredient. As described above, by "lower the GI" or "GI lowering extract" it is meant that the GI of the substance, product or ingredient to which the sugar cane derived extract is added is lowered compared to the GI of the substance, product or ingredient not containing the sugar cane derived extract. It does not have to make the substance itself low GI (i.e. GI<55), although it may in fact do so depending on the substance.

It will be understood that the invention disclosed and defined in this specification extends to all alternative combinations of two or more of the individual features mentioned or evident from the text or drawings. All of these different combinations constitute various alternative aspects of the invention.

The invention is now described with reference to the following non-limiting examples.

Examples

1. Preparation of a Polyphenol Enriched Molasses Extract

An extract was prepared that contained more concentrated, lower molecular weight, naturally occurring polyphenols (as defined herein) relative to the concentration of each of those polyphenols present in sugar cane molasses. In order to prepare an extract of this embodiment of the invention, the starting material is mill molasses obtained from a sugar mill, which produces raw sugar from cane and is HACCP certified. The process, shown in FIG. 1, involves heat treatment of the molasses at 85° C. for a minimum of 30 minutes to precipitate calcium added in the sugar cane juice treatment process at the primary mill. The molasses is diluted with water to 31-35° Brix to reduce viscosity prior to filtration (GEA Process Engineering Pty Ltd, Blackburn, VIC, Australia) which removes suspended solids and other large components, including microorganisms.

Permeate passes directly to an evaporator feed tank, and is concentrated using a flash evaporator plate (APV Søborg, Denmark), recirculating until the syrup reaches 60-65° Brix. The retentate fraction is discarded as waste.

2. Composition and Nutrition Information for Molasses Extract in Comparison to Mill Molasses FIG. 2 illustrates the composition and nutrition information for a molasses extract of the invention in comparison to mill molasses. The permeate prepared in example 1, which represents one preferred extract of the invention, is a brown liquid extract that still contains sugars, but is less dense and less viscous than molasses and is readily pourable. It has the following composition (whereby the range for each component was determined by testing a number of extracts; the average concentration is given in the next column):

| Component | Range | Average |
| --- | --- | --- |
| Polyphenols g CE/100 g | 1.0-1.5 | 1.15 |
| Moisture, g/100 g | 30-45 | 38.4 |
| Energy, (calc) kJ/100 g | 800-1000 | 946 |
| Protein (N × 6.25, g/100 g) | 1-3 | 2.0 |
| Fat, g/100 g | 0.5-1.2 | 0.9 |
| Sucrose, g/100 g | 20-40 | 29.3 |
| Glucose, g/100 g | 3-10 | 5.4 |
| Fructose, g/100 g | 5-10 | 6.0 |
| Total sugars, g/100 g | 28-60 | 40.7 |
| Sodium, mg/100 g | 45-55 | 50 |
| Soluble dietary fibre, g/100 g | 0-1 | 0.3 |
| Ash, g/100 g | 5-10 | 6.1 |
| Total carbohydrate (by difference, g/100 g) | 45-60 | 52.3 |
| Calcium mg/kg | 5000-6000 | 5450 |
| Iron, mg/kg | 70-100 | 89 |
| Magnesium, mg/kg | 1700-2500 | 2000 |
| Potassium, g/kg | 20-40 | 24.5 |

As would be appreciated by the skilled person, the average concentration given for each component is not intended to be limiting. An extract having, for example, 36 g/100 g moisture will achieve the same promise of the invention as 39 g/100 g.

Using LC-MS, the phenolic compounds found in the extract included ferulic acid, orientin, cyanidin-3-O-glucoside, p-coumaric acid, malvidin-glycoside, epigallocatechin and diosmin.

This extract was used in the subsequent examples. Of the polyphenols present in the extract, they are present in higher relative amounts or concentrations compared to the molasses starting material.

The more detailed results are provided in the table in FIG. 2, including a comparison with the mill molasses starting material. The reference methods for determination of each component are as follows:

Colour: ICUMSA Colour, BSES Standard Method 33
Polyphenols: Kim D-O, Jeong S W and Lee C Y. 2003. Antioxidant capacity of phenolic phytochemicals from various cultivars of plums. Food Chemistry 81:321-26. (substituting catechin for gallic acid)
ORAC Value; Cao G, Alessio H and Cutler R. 1993. Oxygen-radical absorbance capacity (ORAC) assay for antioxidants. Free Radic Biol Med 14:303-11. doi:10.1016/0891-5849(93)90027-R. PMID 8458588.

Flavonoids: Lamaison J L and Carnet A. 1991. Teneurs en principaux flavonoides des fleurs de Cratageus monogyna Jacq et de Cratageus Laevigata (Poiret D. C) en Fonction de la vegetation. Plantes Medicineles Phytotherapie 25:12-16.
Glycaemic Index: ISO 26642:2010 Food Products—Determination of Glycaemic Index On the dry basis (db), comparisons of the nutritional composition show sugars content in the molasses extract to be slightly higher than mill molasses. This difference can be explained by the removal of large molecules from the mill molasses in the filtration process for the extract, thereby concentrating the smaller molecules proportionally. The mineral content is comparable in the extract and mill molasses (db) with calcium, magnesium and potassium being nearly identical.

The polyphenol content remaining in the extract is still high relative to other plant food sources such as coloured rice brans (Min and others 2010). The GI of the extract has been determined to be 45±4.

3. GI Testing

A defined and published GI-testing methodology (WHO 1998; Wolever and others 2003) which has been validated using both small experimental studies and large multi-centre human research trials was used throughout the study (Wolever and others 2008). The experimental procedures used in this study were in accordance with international standards for conducting ethical research with humans.

Subjects

For each GI value determination of a test food, a group of 10 healthy, non-smoking people, aged between 18-45 years, mainly of Caucasian ethnicity were recruited from the staff and student population of the University of Sydney. People volunteering to participate in the study were excluded if they were overweight or underweight; were dieting; had impaired glucose tolerance; were suffering from any illness or food allergy; or were regularly taking prescription medication other than standard contraceptive medication.

Test Foods

The reference food in each example was glucose sugar, with a GI of 100. The test foods were (a) glucose syrup and (b) high fructose corn syrup (HFCS), with and without an extract of the invention.

The reference foods and the two test foods were served to the subjects in fixed test portions containing 50 g of digestible (available) carbohydrate. A required amount of 51.4 g pure glucose sugar (Glucodin® powder, Boots Health Care Company, North Ryde, NSW Australia) dissolved in water was used as the reference food and was consumed by each subject on three separate occasions. The test foods of 50.3 g were each consumed by the 10 subjects on one occasion only. All the test foods and reference food were dissolved in 250 g of warm water and refrigerated overnight. The prepared foods were taken from the refrigerator shortly before being served with 250 g of plain water.

Experimental Procedures

In this study, a GI value for each food was determined from a sample size of 10 healthy individuals. The night before each test session, the subjects ate a regular evening meal based on a carbohydrate-rich food, other than legumes, and then fasted for at least 10 hours overnight. The subjects were restricted on their alcohol intake, food intake, and physical activity for the whole day before each test session. Each subject consumed portions of food containing 50 g of available carbohydrate. Foods were consumed evenly over a 12 minute period. The reference food was consumed three times and the test foods were consumed once in a random order. Each test was completed on a separate morning with at least one day in between subsequent test sessions.

Blood Glucose Measurement

Finger-pricked blood samples were obtained (≥0.5 mL blood) using an automatic, non-reusable lancet device (Safe-T-Pro®, Boehringer Mannheim Gmbh, Germany). The blood samples were taken at -5 and 0 minute as a fasting blood sample followed by consumption of reference food or test food. Further blood sample were collected at 15, 30, 45, 60, 90 and 120 minutes after eating had commenced. Each blood sample was centrifuged for 30 seconds immediately after it was collected. The plasma layer of the sample was then collected stored at -20° C. until their glucose concentrations were analysed.

Measurement of Plasma Glucose Concentrations and GI Values

Plasma glucose levels were analysed in duplicates using a glucose hexokinase enzymatic assay (Roche Diagnostic Systems, Sydney, Australia) and an automatic centrifugal spectrophotometric analyser (Roche/Hitachi 912°, Boehringer Mannheim Gmbh, Germany) with internal controls. The area under the curve (AUC) was calculated in order to obtain a single number, which expresses the total increase in blood glucose in that subject as a result of ingesting the food during the two-hour test session. A glycaemic index (GI) value for each test food was then calculated as follows:

$$GI \text{ value } (\%) = \frac{\text{Plasma glucose } AUC \text{ value for test food}}{\text{Average } AUC \text{ value for the equal carbohydrate portion of the reference food}} \times 100$$

Statistical Analysis

Standard parametric statistical tests (Analysis of Variance and the Fisher PLSD test for multiple comparisons) were used to determine whether there were any significant differences between the GI values of the test foods and the reference food. The smaller the p-value, the more significant the difference, with p<0.001 (99.9%) being the most significant difference.

Results (a) Glucose

The means and standard errors of the GI and II for the 2 glucose syrups are shown in Table 4, (extracted from the table in FIG. 3B). No outliers were observed among the GI and II results for either test product, so all means were calculated using all 10 subjects.

TABLE 4

Mean and standard error of GI and II values for the 2 glucose syrups

| Test Food | GI Value | GI Category | II Value |
|---|---|---|---|
| Glucose syrup 41BE | 107 ± 7 | High GI | 105 ± 4 |
| Glucose syrup 41BE + extract | 93 ± 9 | High GI | 87 ± 7 |

(b) HFCS

The means and standard errors of the GI and II for the 2 HFCS samples are shown in Table 5 (extracted from the table in FIG. 3B). No outliers were observed among the GI and II results for either test product, so all means were calculated using all 10 subjects.

TABLE 5

Mean and standard error of GI and II values for the
2 high-fructose corn syrups

| Test Food | GI Value | GI Category | II Value |
|---|---|---|---|
| HFCS | 56 ± 5 | Medium GI | 65 ± 5 |
| HFCS + extract | 50 ± 3 | Low GI | 58 ± 3 |

Addition of an extract of the invention to the monosaccharide glucose, and high fructose corn syrup, lowered the GI as well as insulin response. This indicates that there is a health benefit to adding extracts of the invention to monosaccharides and disaccharides such as glucose and HFCS. These can in turn be used in foods and beverages in place of the standard sweetener

Figure 4:
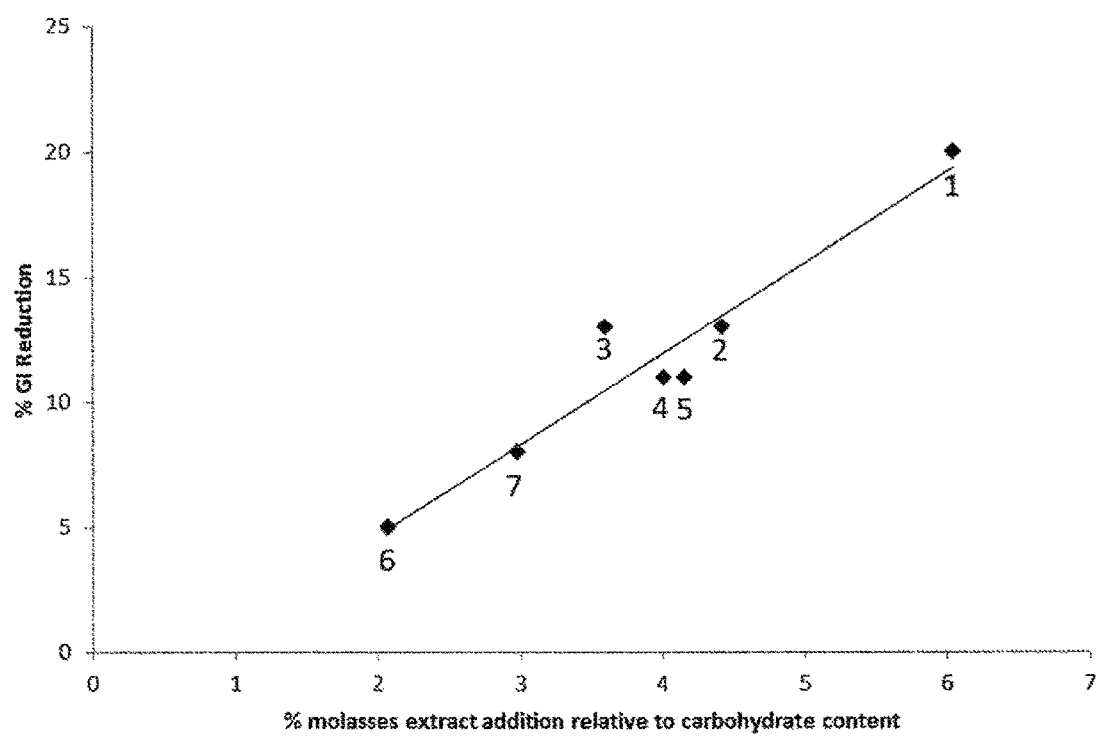
FIG. 4 illustrates the correlation of GI reduction to molasses extract addition, relative to carbohydrate content. As the amount of extract added to the food matrix is increased (relative to carbohydrate content of the food), the glycaemic index (GI) value is reduced (correlation R2=0.922). Foods tested include: 1—white bread, 2—glucose syrup, 3—fruit flavoured beverage, 4—High Fructose Corn Syrup (HFCS), 5—energy bar, 6—wheat flake cereal bricks (1.4 g/100 g), 7—wheat flake cereal bricks (2.0 g/100 g).

4. Polyphenol Enriched Molasses Extract Reduces GI in Food and Beverage Products The addition of extracts of the invention to more complex carbohydrate food and beverage products tested generally resulted in reduction in GI and II. FIG. 3A outlines the foods tested. The ingredients and approximate composition of test products shows the variety in type and amount of carbohydrate, and macronutrient composition. As illustrated in FIG. 3B the addition of the extract produced in Example 1 reduces glucose and insulin responses. Addition of extract reduces glycaemic index (GI) in all food matrices tested. Insulin index (II) is reduced in all food matrices except the energy bar, which contains protein and more fat than other products tested. In comparing the reduction in GI across the range of samples tested, the percentage reduction in GI due to addition of extract does not appear to be directly related to the amount of extract added as a percentage of the total food or beverage matrix. Rather, the reduction in GI is dose-dependent, and directly proportional to the amount of extract added as a percentage of available carbohydrate content (FIG. 4). The linear relationship was consistent across the range of products tested, varying in composition, carbohydrate content, and type of carbohydrate present. This correlation is consistent with previously referenced observations of the effect of polyphenols on carbohydrate metabolism, reducing blood glucose response.

This observation shows that extracts of the invention can reduce the GI of high carbohydrate-containing foods and beverages. The GI will depend on the individual characteristics of each food product such as the degree of starch gelatinization, which is known to have a significant effect (Ross and others 1987).

There was also a corresponding decrease in II among the different foods tested with the exception of an energy bar. The effects on energy bar might be complicated by the other non-carbohydrate ingredients in the energy bar which can affect the insulin index. It is known that certain dairy products can increase insulin levels.

5. The Effects of Polyphenol Enriched Molasses Extract on Postprandial Glucose and Insulin Responses A group of 38 healthy, non-smoking people aged between 18 and 35 years were recruited. People volunteering to participate in the study were excluded if they were over- or underweight, were dieting, had impaired glucose tolerance, were suffering from any illness or food allergy, or were regularly taking prescription medication other than standard contraceptive medication. The subject group consisted of 19 males and 19 females. The mean age of the subjects was 26.8 years (range: 18.6-34.2 years) and the group's mean body mass index (BMI) score was 22.3 kg/m2 (range: 18.9-25.0 kg/m2). The BMI score is a measure of a person's weight in relation to his/her height; values between 18 and 25 kg/m2 are within the healthy weight range.

These 38 subjects ingested the test meal and placebo or 2 doses of molasses extract prepared in accordance with example 1 (3 tests). Fifteen subjects were selected to test two further doses of extract (5 tests total). These fifteen subjects satisfied at least two of the following criteria: age>30 years, BMI>23.5 kg/m2, fasting glucose>5 mmol/L, Matsuda index (calculated from placebo meal)<10.5. These 15 subjects included 9 males and 6 females with a mean age of 30.2 (range 18.8-34.4) and BMI of 23.3 kg/m2 (range: 19.2-25.0 kg/m2).

Meals and Investigational Products

The molasses extract was given as a supplement and was consumed with a standard breakfast meal. All 38 subjects tested Meals 1 to 3; a subset of 15 subjects also tested Meals 4 and 5. The product was given to all subjects in two different doses, 8 g and 22 g, and placebo syrup was used as a control. The 15 subjects performing extra testing also ingested extract doses of 40 g and 60 g.

Each subject consumed the first three meals, each on a separate occasion. The test meals consisted of:
1. Test Meal 1: 30 g placebo syrup consumed with 100 g of white bread, 12 g butter, 65 g scrambled eggs and 170 g orange & mango juice.
2. Test Meal 2: 8 g extract+22 g water consumed with 100 g white bread, 12 g butter, 65 g scrambled eggs and 170 g orange & mango juice.
3. Test Meal 3: 22 g extract+8 g water consumed with 100 g white bread, 12 g butter, 65 g scrambled eggs and 170 g orange & mango juice.

The extra meals tested by 15 subjects during the trial extension consisted of:
1. Test Meal 4: 40 g extract syrup+45 g water consumed with 100 g white bread, 12 g butter, 65 g scrambled eggs and 170 g orange & mango juice.
2. Test Meal 5: 60 g extract+25 g water consumed with 100 g white bread, 12 g butter, 65 g scrambled eggs and 170 g orange & mango juice.

Nutritional information for the standard meal, the placebo and the extract doses is shown in Table 6.

TABLE 6

Macronutrient composition of breakfast meal and doses

| Test Food | Portion size (g) | Energy from product (kJ) | Protein (g) | Fat (g) | Available CHO (g) | Sugar (g) | Fibre (g) |
|---|---|---|---|---|---|---|---|
| Standardized Meal | 347 g | 1999 | 17.3 | 18.1 | 59.1 | 18.4 | 6.6 |

TABLE 6-continued

Macronutrient composition of breakfast meal and doses

| Test Food | Portion size (g) | Energy from product (kJ) | Protein (g) | Fat (g) | Available CHO (g) | Sugar (g) | Fibre (g) |
|---|---|---|---|---|---|---|---|
| Placebo Syrup | 30 g | 95 | 0 | 0 | 5.7 | 5.7 | 0 |
| 8 g extract | 8 g extract + 22 g water | 75 | 0.2 | 0.1 | 4.2 | 3.4 | 0 |
| 22 g extract | 22 g extract + 8 g water | 207 | 0.6 | 0.2 | 11.7 | 9.2 | 0.1 |
| 40 g extract | 40 g extract + 45 g water | 377 | 1 | 0.4 | 21.2 | 16.8 | 0.1 |
| 60 g extract | 60 g extract + 25 g water | 565 | 1.5 | 0.5 | 31.8 | 25.2 | 0.2 |

Study Procedures

The study used a crossover design such that every subject consumed each Test Meal on one occasion only in random order, completing a total of three test sessions. Each subject completed his or her test sessions on separate weekday mornings at a similar time of day, as close as possible to the time at which the subject normally ate breakfast.

The day before each test session, the subjects were to avoid unusual levels of food intake and physical activity, and to refrain from consuming alcohol for the entire day. The night before the test session, they were required to eat a regular evening meal based on a low-fat, carbohydrate-rich food, other than legumes, and then fast for at least 10 hours overnight, until the start of their test session the next morning. During the fasting period, the subjects were only allowed to drink water.

On the day two fasting finger-prick blood samples of ≥0.7 nil (−5 minute and 0 minutes) were obtained. After the second fasting sample (0 minutes) was obtained, the subjects were served one of the breakfast meals, including the extract shot served as a syrup, which they consumed within 12 minutes. The subjects remained at the research centre for the next two hours, during which additional blood samples were collected at 15, 30, 45, 60, 90, and 120 minutes after eating had commenced.

Measurement of Plasma Glucose Concentrations

The glucose concentrations of each subject's plasma samples was calculated by standard methodology and a two-hour plasma response curve constructed using the average glucose concentrations for each of their plasma samples. The two fasting plasma samples of each test session were averaged to provide one baseline glucose concentration. The incremental area under each 2-hour plasma glucose response curve (iAUC) was calculated to obtain a single number expressing the total increase in blood glucose in that subject as a result of ingesting the specific food during the 2-hour test session.

Measurement of Plasma Insulin Concentrations

For each subject, the concentration of insulin in each of the 8 plasma samples was calculated by standard methodology. The two fasting blood samples were averaged to provide one baseline insulin concentration. A two-hour plasma insulin curve was then constructed for each subjects test sessions and the incremental area under the curve (iAUC) was calculated.

Results a) Plasma Glucose Levels for Meals 1 to 3

Figure 5:
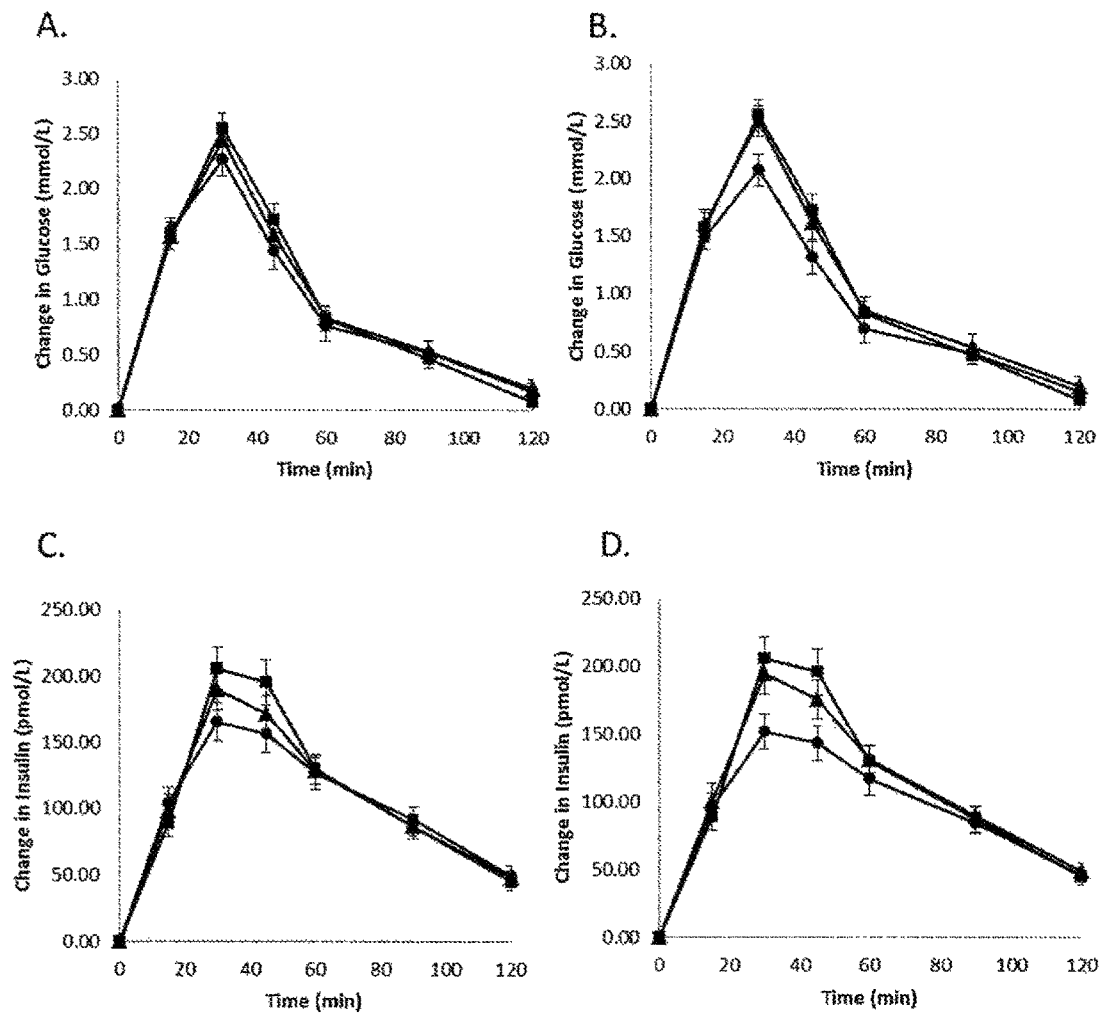
FIG. 5: Glucose and insulin responses to molasses extract. (A). Plasma glucose change over 2 hour period (mean±SEM; n=38) after ingestion of standardized breakfast meal with a molasses extract taken before meal: placebo (squares), 8 g of extract (triangles) or 22 g of extract (circles). (B). Plasma glucose change standardised for carbohydrate ingestion (arbitrarily adjusted to 64.8 g, amount ingested during placebo test) over 2 hour period (mean±SEM; n=38) after ingestion of standardized breakfast meal with a molasses extract syrup supplement taken before meal: placebo (squares), 8 g of extract (triangles) or 22 g of extract (circles). (C). Plasma insulin change (mean±SEM; n=38) over 2 hour period after ingestion of standardized breakfast meal with a molasses extract syrup supplement taken before meal: placebo (squares), 8 g of extract (triangles) or 22 g of extract (circles). (D). Plasma insulin change standardised for carbohydrate ingestion (arbitrarily adjusted to 64.8 g, amount ingested during placebo test) over 2 hour period (mean±SEM; n=38) after ingestion of standardized breakfast meal with a molasses extract syrup supplement taken before meal: placebo (squares), 8 g of extract (triangles) or 22 g of extract (circles).

The average two-hour plasma glucose response curves for the placebo breakfast Test Meal and the two Test Meals containing 8 g and 22 g extract are shown in FIG. 5A. The overall shape of the glycaemic response curves was similar for the three test meals. All three meals produced a steady initial rise in glucose level to a moderate peak response at 30 minutes, followed by a steady decline in glucose concentration between 30 and 120 minutes. Test Meal 3 (22 g extract) produced a lower plasma glucose concentration between 30 and 60 minutes compared to the other two Test Meals, resulting in the lowest overall glycaemic response during the experimental period, even though Test Meal 3 contained the highest level of total energy.

In post-hoc analysis, when all treatments were normalised to equal amounts of available carbohydrate (arbitrarily set at 64.8 g, the amount of carbohydrate in the placebo treatment, FIG. 5B) there is both a treatment effect ($p<0.005$) and a time by treatment effect ($p=0.001$). The normalised change value at 30 minutes was significantly lower with the 22 g extract dose (2.07 mmol/L) compared to the placebo (2.55 mmol/L) and 8 g extract (2.50 mmol/L) treatments (both $p<0.005$) while the value at 45 minutes with 22 g extract (1.32 mmol/L) was also significantly lower than placebo (111 mmol/L, $p<0.005$). Peak change values, when adjusted for carbohydrate, showed a significant treatment effect ($p<0.001$) with the peak value in response to the 22 g extract dose (2.30 mmol/L) significantly lower than both the placebo (2.66 mmol/L; $p<0.001$) and 8 g extract (2.67 mmol/L; $p<0.001$) treatments.

b) Plasma Insulin Levels for Meals 1 to 3

The mean two-hour plasma insulin response curves for the placebo breakfast meal and the two meals containing different doses of extract syrup are shown in FIG. 5C and responses standardised to carbohydrate level are shown in FIG. 5D. The overall shape of the insulinaemic response curves was similar for the three Test Meals; however, the magnitude of the responses differed among the meals. All three meals showed a steady rise in plasma insulin to a peak concentration at 30 minutes, followed by a gradual decline in insulin level between 30 and 120 minutes. There is a treatment effect for both absolute values ($p<0.01$) and carbohydrate standardised values ($p<0.005$) as well as a time by treatment effect with standardised values ($p<0.0001$). As with the plasma glucose response, overall peak insulin increase was influenced by the 22 g extract dose ($p<0.02$) with a reduction from 252 pmol for placebo to 211 pmol/L. When standardised to equivalent carbohydrate intakes the treatment effect was greater ($p<0.001$).

Discussion of Results of (a) and (b)

Neither the glucose nor insulin incremental areas under the curve (iAUC) were significantly different between any of the meals when analysed with parametric repeated-measures ANOVA. The glucose and insulin values at times 30 min and 45 min were significantly different (p<0.05) between meal 1 (placebo) and meal 3 (22 g Benecarb) despite the increase in total carbohydrate in meal 3. The mean reduction in insulin response for all subjects was dose-dependent and linearly proportional to the amount of Benecarb ingested, almost a 1% reduction in peak insulin response per gram of Benecarb (Table 7).

TABLE 7

| | | All subjects (n = 38) | | |
|---|---|---|---|---|
| | Treatment | Mean | SEM | % change[a] |
| Peak Insulin Response (pmol/L) | Placebo | 251.6 | 16.1 | — |
| | 8 g extract | 230.7 | 13.0 | −9 |
| | 22 g extract | 211.1** | 12.9 | −9 |
| Insulin iAUC (pmol/L · min) | Placebo | 13554 | 846 | — |
| | 8 g extract | 13103 | 810 | −3 |
| | 22 g extract | 12766 | 951 | −3 |

[a]% change, change relative to preceding dose level (8 g relative to placebo; 22 g relative to 8 g)

However, resveratrol and other polyphenol based therapies have little effect on people with normal glucose blood chemistry while they do have a significant impact on individuals with impaired glucose tolerance. Accordingly, we re-analysed the data on the basis of the 38 being grouped according to risk parameters such as age, BMI and fasting glucose levels. When subjects were stratified based on age, BMI, Matsuda Index or fasting glucose levels there were significant treatment and/or time by treatment effects on insulin response only in those groups classified as being at higher risk of increased insulin resistance. Less at risk groups displayed no reduction in insulin response with 8 g of extract relative to placebo response whilst those in the more at risk groups had up to a 19% reduction in peak insulin response and a 15% reduction in insulin incremental area under the curve (iAUC). Reduction in insulin response was almost identical for all subgroups between the 8 g and 22 g extract doses.

Figure 6:
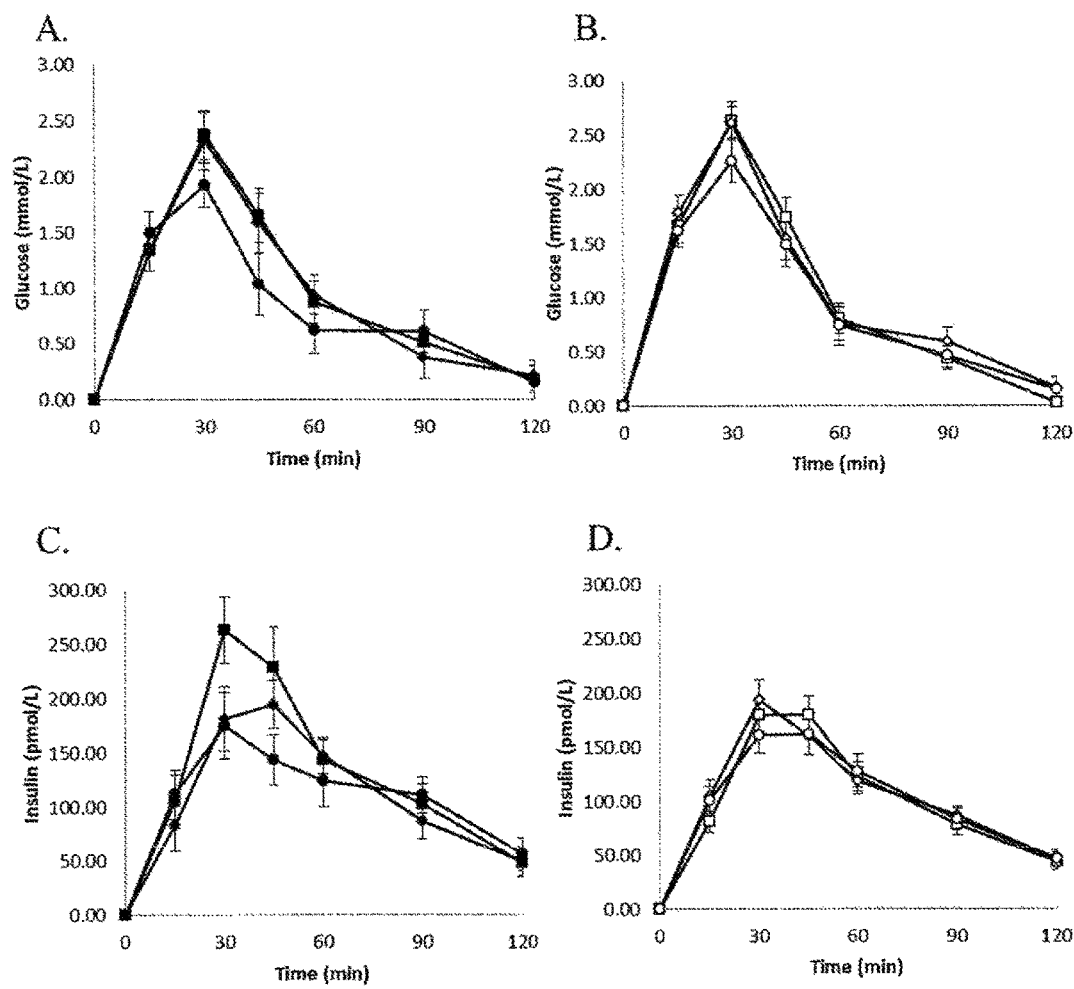
FIG. 6. Glucose and insulin responses to molasses extract subgrouped by BMI. (A). Plasma glucose change for subjects with BMI>23.5 over 2 hour period (mean±SEM; n=12) after ingestion of standardized breakfast meal with a molasses extract taken before meal: placebo (closed squares), 8 g of extract (closed triangles) or 22 g of extract (closed circles). (B). Plasma glucose change for subjects with BMI≤23.5 over 2 hour period (mean±SEM; n=26) after ingestion of standardized breakfast meal with a molasses extract taken before meal: placebo (open squares), 89 of extract (open triangles) or 22 g of extract (open circles), (C). Plasma insulin change for subjects with BMI>23.5 over 2 hour period (mean±SEM; n=12) after ingestion of standardized breakfast meal with a molasses extract taken before meal: placebo (closed squares), 8 g of extract (closed triangles) or 22 g of extract (closed circles). (D). Plasma insulin change for subjects with BMI≤23.5 over 2 hour period (mean±SEM; n=26) after ingestion of standardized breakfast meal with a molasses extract taken before meal: placebo (open squares), 8 g of extract (open triangles) or 22 g of extract (open circles).
Figure 7:
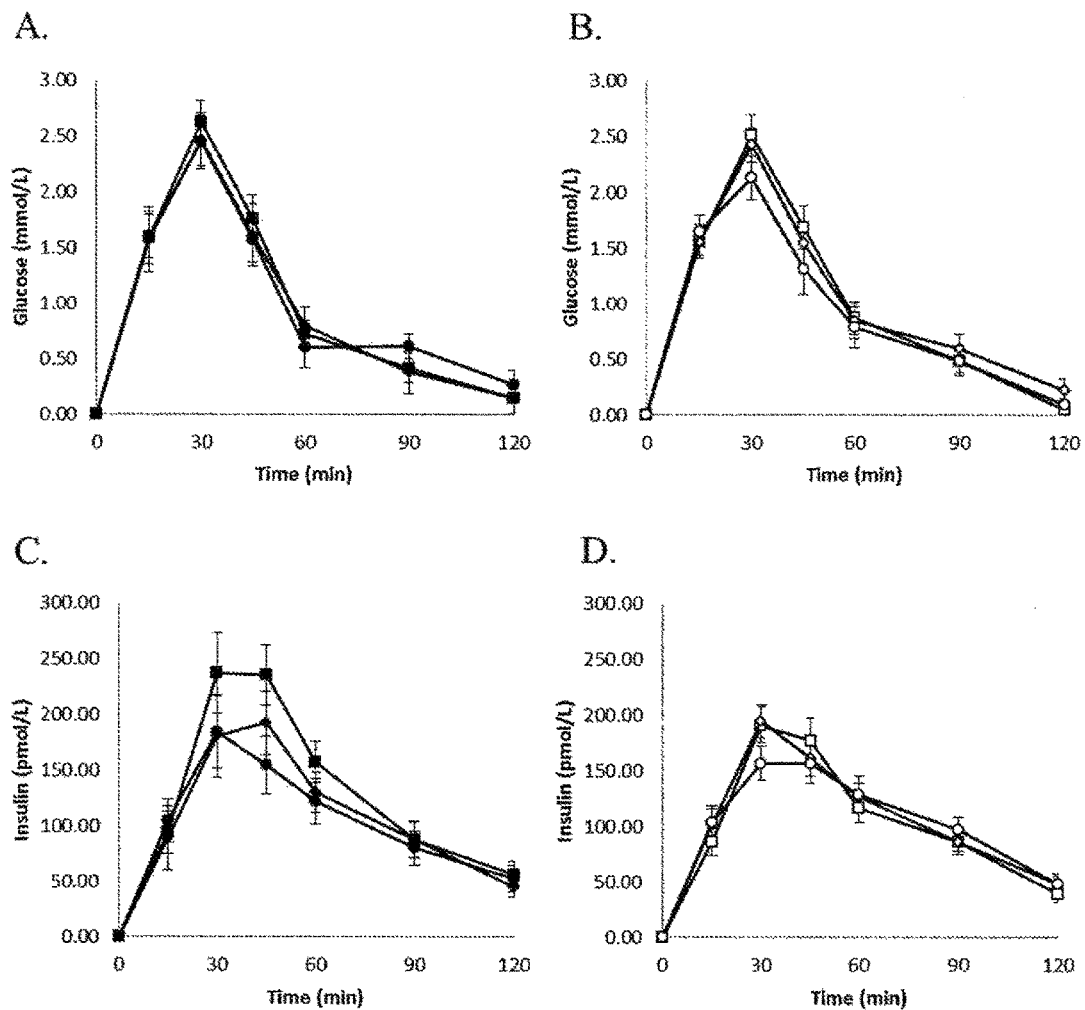
FIG. 7. Glucose and insulin responses to molasses extract subgrouped by age. (A). Plasma glucose change for subjects with age>30 years over 2 hour period (mean±SEM; n=12) after ingestion of standardized breakfast meal with a molasses extract taken before meal: placebo (closed squares), 8 g of extract (closed triangles) or 22 g of extract (closed circles). (B). Plasma glucose change for subjects with age≤30 years over 2 hour period (mean±SEM; n=26) after ingestion of standardized breakfast meal with a molasses extract taken before meal: placebo (open squares), 8 g of extract (open triangles) or 22 g of extract (open circles). (C). Plasma insulin change for subjects with age>30 years over 2 hour period (mean±SEM; n=12) after ingestion of standardized breakfast meal with a molasses extract taken before meal: placebo (closed squares), 8 g of extract (closed triangles) or 22 g of extract (closed circles). (D). Plasma insulin change for subjects with age≤30 years over 2 hour period (mean±SEM; n=26) after ingestion of standardized breakfast meal with a molasses extract taken before meal: placebo (open squares), 8 g of extract (open triangles) or 22 g of extract (open circles).
Figure 8:
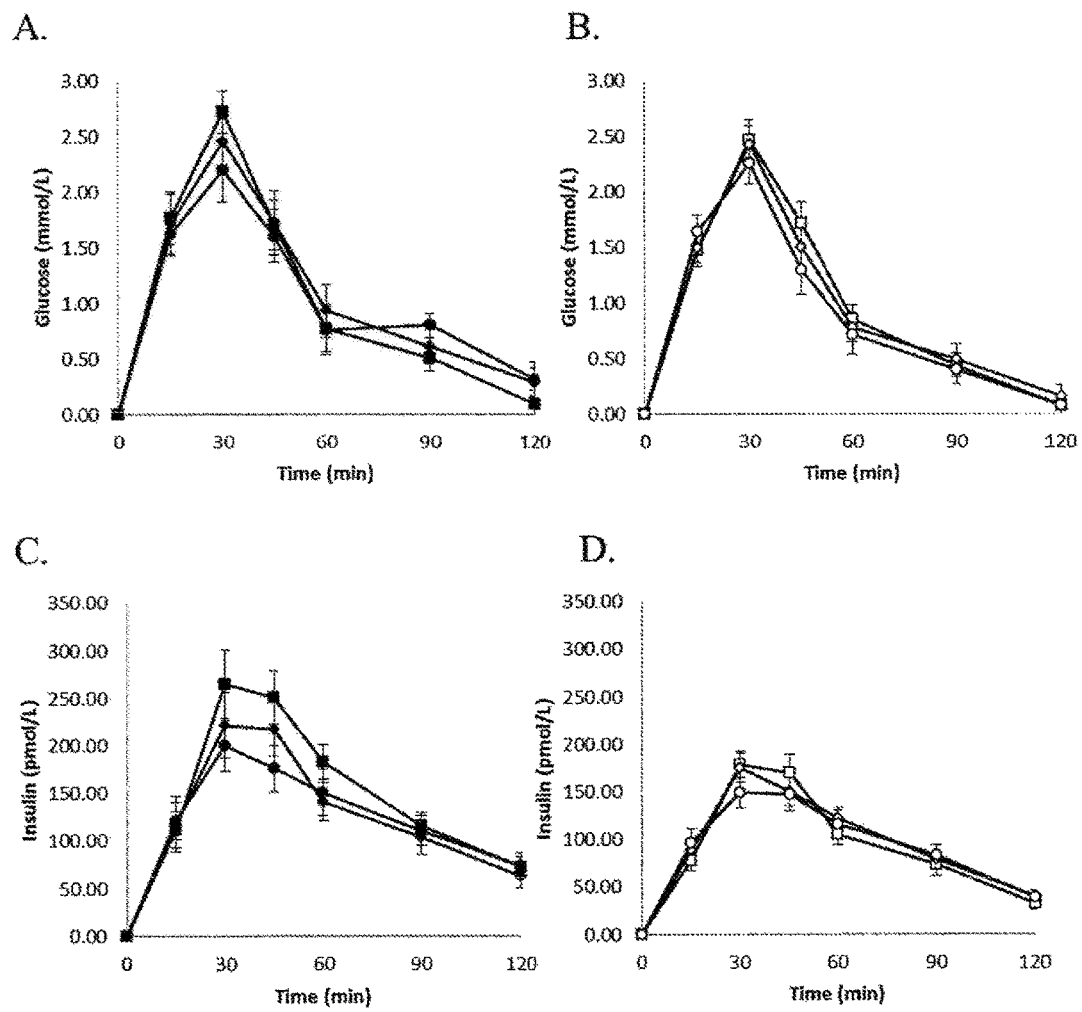
FIG. 8. Glucose and insulin responses to molasses extract subgrouped by fasting glucose (FG). (A). Plasma glucose change for subjects with FG≥5.24 mmol/L over 2 hour period (mean±SEM; n=14) after ingestion of standardized breakfast meal with a molasses extract taken before meal: placebo (closed squares), 8 g of extract (closed triangles) or 22 g of extract (closed circles). (B). Plasma glucose change for subjects with FG<5.24 mmol/L over a 2 hour period (mean±SEM; n=24) after ingestion of standardized breakfast meal with a molasses extract taken before meal: placebo (open squares), 8 g of extract (open triangles) or 22 g of extract (open circles). (C). Plasma insulin change for subjects with FG≥5.24 mmol/L over 2 hour period (mean±SEM; n=14) after ingestion of standardized breakfast meal with a molasses extract taken before meal: placebo (closed squares), 8 g of extract (closed triangles) or 22 g of extract (closed circles). (D). Plasma insulin change for subjects with FG<5.24 mmol/L over a 2 hour period (mean±SEM; n=24) after ingestion of standardized breakfast meal with a molasses extract taken before meal: placebo (open squares), 8 g of extract (open triangles) or 22 g of extract (open circles).

FIG. 6 and Table 8 shows glucose (6A and B) and insulin (6C and D) responses parsed depending on BMI (>23.5 kg/m2 vs.≤23.5 kg/m2). Higher BMI subjects have a higher average insulin response to the placebo meal compared to lower BMI subjects. After consumption of the high dose extract meal 3 (22 g extract) the glucose and insulin responses were reduced in the higher risk group, but essentially unchanged in the lower BMI group. This suggests that the molasses extract of the invention is beneficial to subjects at higher risk of developing diabetes or type 2 diabetes.

TABLE 8

| | | BMI > 23.5 kg/m2 (n = 12) | | |
|---|---|---|---|---|
| | Treatment | Mean | SEM | % change[a] |
| Peak Insulin Response (pmol/L) | Placebo | 302.7 | 36.0 | — |
| | 8 g extract | 241.7 | 24.2 | −20 |
| | 22 g extract | 220.1* | 25.1 | −9 |
| Insulin iAUC (pmol/L · min) | Placebo | 16014 | 1753 | — |
| | 8 g extract | 13568* | 1407 | −15 |
| | 22 g extract | 13463* | 1889 | −1 |
| | | BMI ≤ 23.5 kg/m2 (n = 26) | | |
| | Treatment | Mean | SEM | % change[a] |
| Peak Insulin Response (pmol/L) | Placebo | 224.4 | 14.8 | — |
| | 8 g extract | 223.9 | 16.0 | 0 |
| | 22 g extract | 206.6 | 15.2 | −8 |
| Insulin iAUC (pmol/L · min) | Placebo | 12418 | 872 | — |
| | 8 g extract | 12889 | 1005 | +4 |
| | 22 g extract | 12444 | 1104 | −3 |

[a]% change, change relative to preceding dose level (8 g relative to placebo; 22 g relative to 8 g)
Significantly different from placebo, *p < 0.05, p < 0.01, *p < 0.005

Similarly, when the subject pool was parsed according to age the higher risk subjects (age≥30 years) had a more pronounced response to the extract treatment than the lower risk subjects (FIG. 7A-D and Table 9 below).

TABLE 9

| | | Age > 30 years (n = 12) | | |
|---|---|---|---|---|
| | Treatment | Mean | SEM | % change[a] |
| Peak Insulin Response (pmol/L) | Placebo | 283.8 | 33.3 | — |
| | 8 g extract | 228.5*,[b] | 30.8 | −19 |
| | 22 g extract | 205.7** | 28.4 | −10 |
| Insulin iAUC (pmol/L · min) | Placebo | 15551 | 1737 | — |
| | 8 g extract | 13202 | 1847 | −15 |
| | 22 g extract | 12616** | 1892 | −4 |
| | | Age ≤ 30 years (n = 26) | | |
| | Treatment | Mean | SEM | % change[a] |
| Peak Insulin Response (pmol/L) | Placebo | 233.2 | 17.4 | — |
| | 8 g extract | 231.3 | 13.2 | −1 |
| | 22 g extract | 213.2 | 14.0 | −8 |
| Insulin iAUC (pmol/L · min) | Placebo | 12632 | 909 | — |
| | 8 g extract | 13058 | 851 | +3 |
| | 22 g extract | 12835 | 1108 | −2 |

[a]% change, change relative to preceding dose level (8 g relative to placebo; 22 g relative to 8 g)
Significantly different from placebo, *p < 0.05, p < 0.01, *p < 0.005

When subjects were divided according to their fasting glucose values, those with higher values (fasting glucose>5.24 mmol/L in this example) had a stronger reduction in glucose and insulin levels than those subjects with fasting glucose levels<5.24 mmol/L (FIG. 8A-D and Table 10),

TABLE 10

| | | FG ≥ 5.24 mmol/L (n = 14) | | |
|---|---|---|---|---|
| | Treatment | Mean | SEM | % change |
| Peak Insulin Response (pmol/L) | Placebo | 273.7 | 23.2 | — |
| | 8 g extract | 237.3 | 12.8 | −13 |
| | 22 g extract | 219.4* | 15.1 | −8 |
| Insulin iAUC (pmol/L · min) | Placebo | 14628 | 1411 | — |
| | 8 g extract | 13572 | 1172 | −7 |
| | 22 g extract | 13471 | 1354 | −1 |
| | | FG < 5.24 mmol/L (n = 24) | | |
| | | Mean | SEM | % change |
| Peak Insulin Response (pmol/L) | Placebo | 238.7 | 21.6 | — |
| | 8 g extract | 226.8 | 19.4 | −5 |
| | 22 g extract | 206.2 | 18.7 | −9 |
| Insulin iAUC (pmol/L · min) | Placebo | 12927 | 1058 | — |
| | 8 g extract | 12830 | 1099 | −1 |
| | 22 g extract | 12354 | 1296 | −4 |

Figure 9:
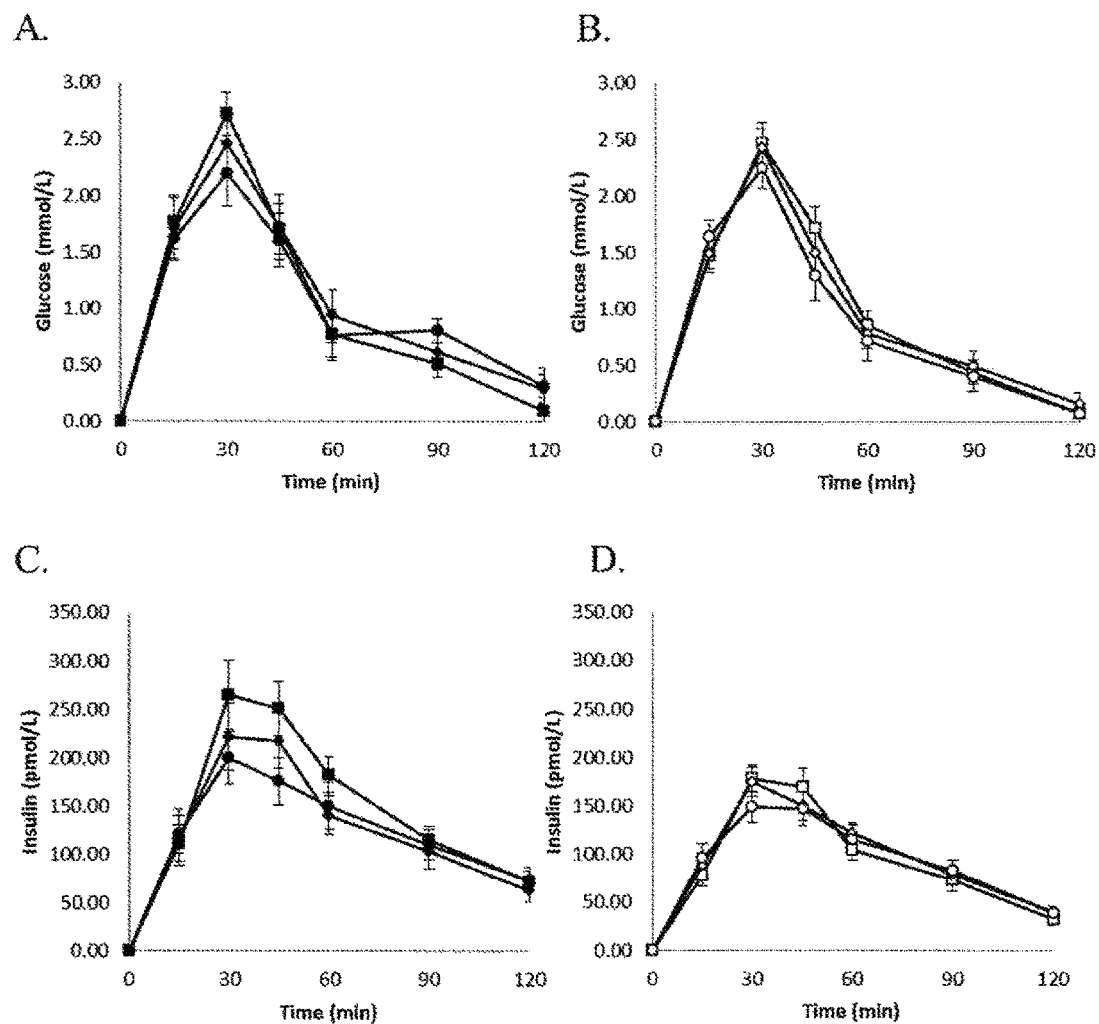
FIG. 9. Glucose and insulin responses to molasses extract subgrouped by Matsuda Index (MI). (A). Plasma glucose change for subjects with MI<10.5 over 2 hour period (mean±SEM; n=12) after ingestion of standardized breakfast meal with a molasses extract taken before meal: placebo (closed squares), 8 g of extract (closed triangles) or 22 g of extract (closed circles). (B). Plasma glucose change for subjects with MI>10.5 over 2 hour period (mean±SEM; n=26) after ingestion of standardized breakfast meal with a molasses extract taken before meal: placebo (open squares), 8 g of extract (open triangles) or 22 g of extract (open circles). (C). Plasma insulin change for subjects with MI<10.5 over 2 hour period (mean±SEM; n=12) after ingestion of standardized breakfast meal with a molasses extract taken before meal: placebo (closed squares), 8 g of extract (closed triangles) or 22 g of extract (closed circles). (D). Plasma insulin change for subjects with MI>10.5 over 2 hour period (mean±SEM; n=26) after ingestion of standardized breakfast meal with a molasses extract taken before meal: placebo (open squares), 8 g of extract (open triangles) or 22 g of extract (open circles).

Sub grouping according to the Matsuda Index (which is a calculation of insulin sensitivity) value in response to meal 1 (placebo) produced similar effects. FIG. 9 and Table 11 shows that the extract had a more pronounced effect on the blood glucose (9A and B) and insulin (9C and D) levels in low Matsuda Index subjects (who are more insulin resistant) than those with higher Matsuda Index subjects (more insulin sensitive).

TABLE 11

| | | Mat. Ind. < 10.5 (n = 12) | | |
|---|---|---|---|---|
| | Treatment | Mean | SEM | % change[a] |
| Peak Insulin Response (pmol/L) | Placebo | 320.2 | 26.8 | — |
| | 8 g extract | 255.4* | 31.5 | −20 |
| | 22 g extract | 234.2*** | 24.8 | −8 |
| Insulin iAUC (pmol/L · min) | Placebo | 18092 | 1326 | — |
| | 8 g extract | 15596 | 1914 | −14 |
| | 22 g extract | 15288* | 1692 | −2 |
| | | Mat. Ind. > 10.5 (n = 26) | | |
| | Treatment | Mean | SEM | % change[a] |
| Peak insulin Response (pmol/L) | Placebo | 219.9 | 17.1 | — |
| | 8 g extract | 219.3 | 12.2 | 0 |
| | 22 g extract | 200.0 | 14.9 | −9 |
| Insulin iAUC (pmol/L · min) | Placebo | 11459 | 797 | — |
| | 8 g extract | 11953 | 711 | +4 |
| | 22 g extract | 11602 | 1097 | −3 |

[a]% change, change relative to preceding dose level (8 g relative to placebo; 22 g relative to 8 g)
Significantly different from placebo, *$p < 0.05$, $p < 0.01$, *$p < 0.005$ As the effect of an extract of the invention is more pronounced on individuals further along the spectrum towards prediabetes/diabetes this suggests a more systemic effect than simple restriction of glucose entering the blood. A general role in inhibiting glycolytic enzymes or intestinal glucose transport should theoretically effect subjects similarly regardless of metabolic status.

Trial Extension

The differential effect of polyphenol enriched extract supplementation on subjects further along the diabetic spectrum suggested a trial extension with higher doses of the extract in a subset of the subjects who are most likely to respond positively to supplementation (FIG. 10), 15 of the original 38 subjects were selected based on their inclusion in two or more subgroups at higher risk: age>30 years, BMI>23.5 kg/m2. Matsuda Index<10.5 and fasting glucose>5 mmol/L.

a) Plasma Glucose Levels for Meals 1 to 5 in 15 Subjects

The average two-hour plasma glucose response curves for the placebo breakfast Test Meal and the four Test Meals containing 8 g, 22 g, 40 g and 60 g extract are shown in FIGS. 10A and B. The overall shape of the glycaemic response curves was similar for the three test meals. All five meals produced a steady initial rise in glucose level to a moderate peak response at 30 minutes, followed by a steady decline in glucose concentration between 30 and 120 minutes. Test Meal 3 (22 g extract) produced a lower plasma glucose concentration between 30 and 60 minutes compared to the other four Test Meals, resulting in the lowest overall glycaemic response during the experimental period. Test meals 4 and 5 had considerably more carbohydrate content than Meal 1 (placebo).

b) Plasma Insulin Levels for Meals 1 to 5 in 15 Subjects

The mean two-hour plasma insulin response curves for the placebo breakfast meal and the two meals containing different doses of extract are shown in FIGS. 10C and D. The overall shape of the insulinaemic response curves was similar for the five Test Meals; however, the magnitude of the responses differed among the meals. All 5 meals showed a steady rise in plasma insulin to a peak concentration at 30 mins, followed by a gradual decline in insulin level between 30 and 120 mins. Insulin response was dose dependent: Test Meal 5 (60 g extract) produced the lowest peak and overall insulinaemic response despite having the highest total energy level, followed by Test Meal 4 (40 g extract). Test Meal 1 (placebo) produced the highest overall insulinaemic response.

As shown in Tables 7-10, the 8 g dose of extract causes a much greater reduction in peak insulin response and in insulin iAUC in the more at-risk groups of older, higher BMI, higher fasting glucose or lower Matsuda Index subjects. The reciprocal, potentially less insulin resistant, groups essentially had no response to the 8 g extract dose. All eight subgroups, as well as the whole subject population, had an 8-10% reduction in peak insulin response between the 8 g and 22 g doses of extract, suggesting the reduction in insulin between the 8 g and 22 g doses is independent of metabolic state. This is also shown in FIG. 11 where the at-risk subjects included in the extended study had an almost 40% higher insulin response to placebo than those subjects not included in the extended study. However, the 8 g and 22 g iAUC values for both groups were within 5% of each other. This suggests 2 different actions attributable to the extract, one having the same effect in all subject groups regardless of metabolic state at doses of 22 g or higher and the second, seen at the low extract dose, reduces insulin responses only in subgroups more at risk of insulin resistance with little to no effect on the less at risk groups (FIG. 11).

Figure 10:
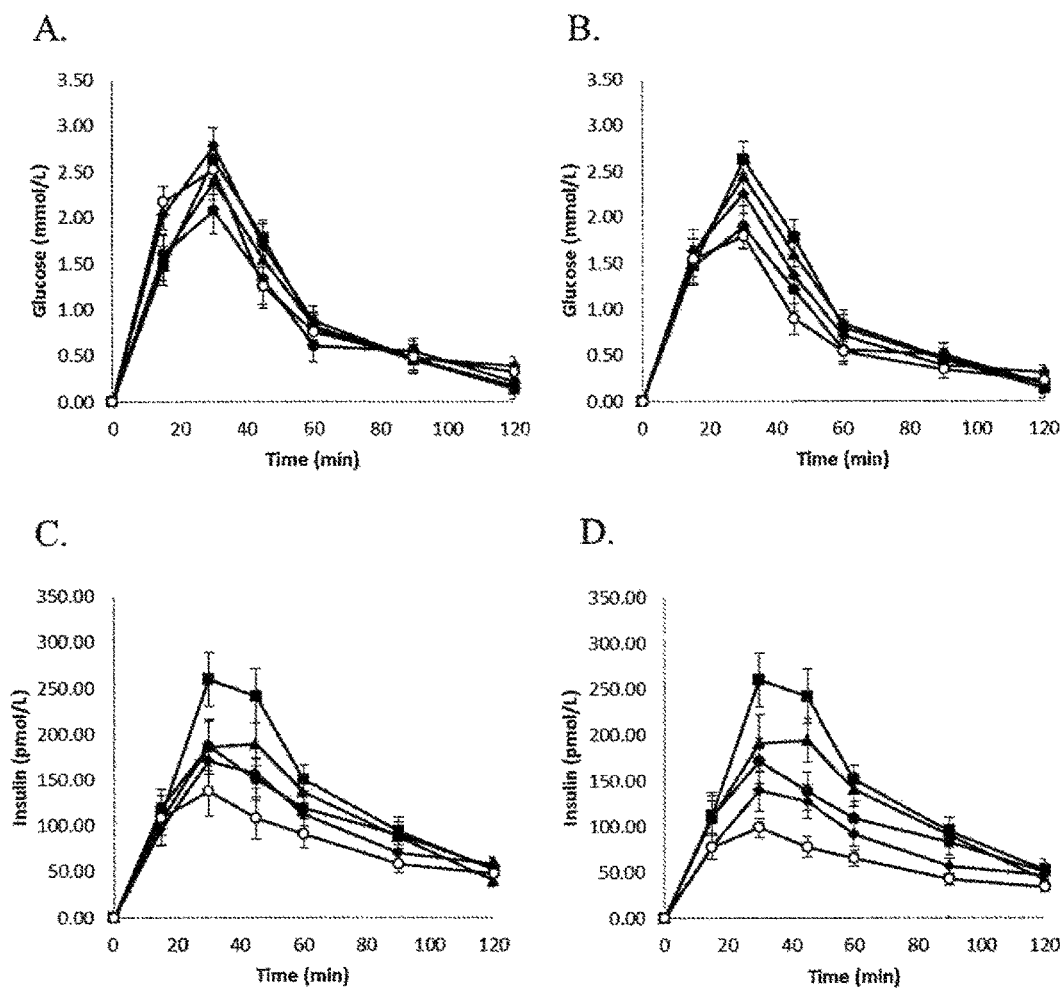
FIG. 10: Glucose and insulin responses to molasses extract—Extended Study. (A) Plasma glucose change over 2 hour period (mean±SEM; n=15) after ingestion of standardized breakfast meal with a syrup supplement taken before meal: placebo (squares), 8 g of extract (triangles), 22 g of extract (closed circles), 40 g of extract (diamonds) and 60 g extract (open circles). (B) Plasma glucose change standardised for carbohydrate ingestion (arbitrarily adjusted to 64.8 g, amount ingested during placebo test) over 2 hour period (mean±SEM; n=15) after ingestion of standardized breakfast meal with a syrup supplement taken before meal: placebo (squares), 8 g of extract (triangles) or 22 g of extract (circles), 22 g of extract (closed circles), 40 g of extract (diamonds) and 60 g extract (open circles). (C) Plasma insulin change (mean±SEM; n=15) over 2 hour period after ingestion of standardized breakfast meal with a syrup supplement taken before meal: placebo (squares), 8 g of extract (triangles), 22 g of extract (closed circles), 40 g of extract (diamonds) and 60 g extract (open circles). (D) Plasma insulin change standardised for carbohydrate ingestion (arbitrarily adjusted to 64.8 g, amount ingested during placebo test) over 2 hour period (mean±SEM; n=15) after ingestion of standardized breakfast meal with a syrup supplement taken before meal: placebo (squares), 8 g of extract (triangles), 22 g of extract (closed circles), 40 g of extract (diamonds) and 60 g of extract (open circles).
Figure 12:
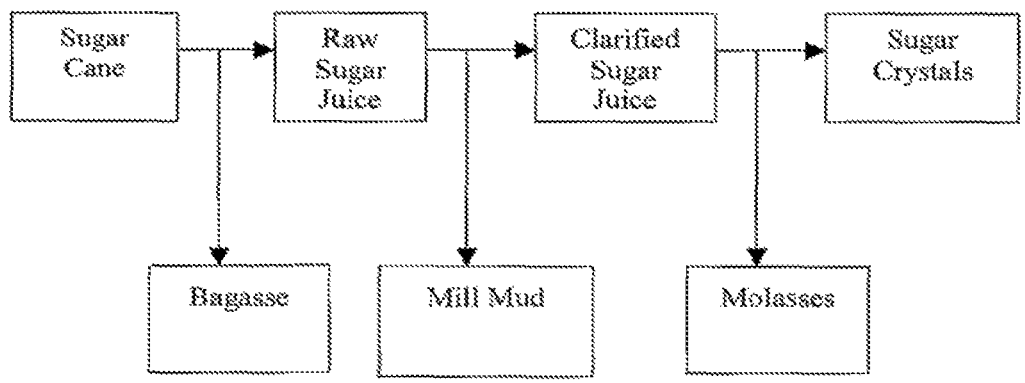
FIG. 12 is a flow chart summarizing the processing of sugar cane.

As can therefore be seen from FIG. 10 a sugar derived extract of the invention lowers postprandial glucose and insulin. And in doing so, it can be seen from FIG. 10B and FIG. 10D, which show the greatest reduction in glucose being a 25% reduction in iAUC, adjusted for carbohydrate content, and the greatest reduction in insulin being a 56% reduction in iAUC, adjusted for carbohydrate content, that the regulation of those 2 responses by an extract of the invention does so without resulting in hypoglycaemia caused by elevated insulin levels.

The invention claimed is:

1. A method for treating a subject having a condition associated with insulin resistance, or for treating a subject predisposed to a condition associated with insulin resistance, comprising the administration of a sugar cane derived extract enriched in polyphenols to the subject, wherein the administration of the sugar cane derived extract lowers postprandial glucose response and insulin response without leading to hypoglycaemia; and wherein the sugar cane derived extract enriched in polyphenols comprises polyphenols in an amount of 20-30 g catechin equivalents (CE)/100 g of extract.

2. A method according to claim 1 wherein the condition associated with insulin resistance is obesity or diabetes.

3. A method according to claim 2 wherein the condition associated with insulin resistance is type 2 diabetes.

4. A method according to claim 1 wherein the sugar cane derived extract enriched in polyphenols is derived from molasses or dunder.

5. A method according to claim 1 wherein the sugar cane derived extract enriched in polyphenols includes no more than 1% total sugars.

6. A method according to claim 1 wherein the sugar cane derived extract enriched in polyphenols comprises a higher relative abundance of smaller molecular weight polyphenols of 30 kDa or less compared to the sugar cane derived product from which it is extracted.

7. A method according to claim 6 wherein the sugar cane derived extract is administered as a capsule or tablet.

8. A method according to claim 1 wherein the sugar cane derived extract enriched in polyphenols comprises a higher relative abundance of hydrophobic polyphenols compared to the sugar cane derived product from which it is extracted.

9. A method according to claim 1 wherein the sugar cane derived product is subjected to hydrophobic chromatography.

10. A method according to claim 1 wherein the sugar cane derived extract enriched in polyphenols comprises one or more of the following polyphenols: p-coumaric acid, ferulic acid, syringic acid, caffeic acid, chlorogenic acid, (−) epicatechin, apigenin, (+) catechin, quercetin, diosmin, rutin, shaftoside, tricin, hydroxyl propanone, orientin, cyanidin-3-O-glucoside, luteolin, diosmetin, vitexin, malvidin-glycoside, petunidin rhamnoside, epigallocatechin and derivatives and mixtures thereof.

11. A method according to claim 1 wherein the sugar cane derived extract enriched in polyphenols comprises the following polyphenols: syringic acid, chlorogenic acid and diosmin and derivatives thereof.

12. A method according to claim 1 wherein the sugar cane derived extract comprises the following:

| Component | |
|---|---|
| Polyphenols (g CE/100 g) | 20-30 |
| Moisture, g/100 g | 3-8 |
| Energy, (calc) kJ/100 g | 1500-2500 |
| Protein (N × 6.25, g/100 g) | 10-15 |
| Fat, g/100 g | 0-0.2 |
| Sucrose, g/100 g | 0-0.2 |
| Glucose, g/100 g | 0-0.2 |
| Fructose, g/100 g | 0-0.2 |
| Total sugars, g/100 g | 0-1 |
| Sodium, mg/100 g | 1-10 |
| Soluble dietary fibre, g/100 g | 0-1 |
| Ash, g/100 g | 0-5 |
| Total carbohydrate (by difference, g/100 g) | 70-90 |
| Calcium, mg/kg | 7000-9500 |
| Iron, mg/kg | 1200-1600 |
| Magnesium, mg/kg | 2200-2700 |
| Potassium, mg/kg | 250-350. |

13. A method according to claim 12 wherein the sugar cane derived extract comprises the following:

| Component | |
|---|---|
| Polyphenols (g CE/100 g) | 23 |
| Moisture, g/100 g | 5 |
| Energy, (calc) kJ/100 g | 1800 |
| Protein (N × 6.25, g/100 g) | 13 |
| Fat, g/100 g | 0.1 |
| Sucrose, g/100 g | 0.1 |
| Glucose, g/100 g | 0.1 |
| Fructose, g/100 g | 0.1 |
| Total sugars, g/100 g | 0.5 |
| Sodium, mg/100 g | 6 |
| Soluble dietary fibre, g/100 g | 0.1 |
| Ash, g/100 g | 3.4 |
| Total carbohydrate (by difference, g/100 g) | 79 |
| Calcium, mg/kg | 8800 |
| Iron, mg/kg | 1400 |
| Magnesium, mg/kg | 2400 |
| Potassium, mg/kg | 290. |

14. A method according to claim 1, wherein the subject is predisposed to insulin resistance and the conditions that result if the subject has one or more risk factors for insulin resistance selected from the group consisting of: being over the age of 30; having a body mass index (BMI) greater than 23; having fasting glucose levels above 5 mmol/L; elevated insulin resistance, and combinations thereof.

15. A method according to claim 1 wherein the method further comprises a step of diagnosing the subject as having a condition associated with insulin resistance or as having a predisposition to insulin resistance and conditions that result, prior to the administration of the sugar cane derived extracts.

16. A method according to claim 1 wherein the sugar cane derived extract is administered as a syrup or powder or added to a food, food ingredient, beverage, dietary supplement, or medical food.

17. A method according to claim 16 wherein the sugar cane derived extract is administered as a dietary supplement, wherein the dietary supplement comprises the sugar cane derived extract and a pharmaceutically acceptable carrier, excipient or diluent.

18. A method for treating a subject having a condition associated with insulin resistance, or for treating a subject predisposed to a condition associated with insulin resistance, comprising the administration of a sugar cane derived extract enriched in polyphenols to the subject, wherein the administration of the sugar cane derived extract lowers postprandial glucose response and insulin response without leading to hypoglycaemia and wherein the sugar cane derived extract comprises the following:

| Component | |
|---|---|
| Polyphenols g CE/100 g | 1.0-1.5 |
| Moisture, g/100 g | 30-45 |
| Energy, (calc) kJ/100 g | 800-1000 |
| Protein (N × 6.25, g/100 g) | 1-3 |
| Fat, g/100 g | 0.5-1.2 |
| Sucrose, g/100 g | 20-40 |
| Glucose, g/100 g | 3-10 |
| Fructose, g/100 g | 5-10 |
| Total sugars, g/100 g | 28-60 |
| Sodium, mg/100 g | 45-55 |
| Soluble dietary fibre, g/100 g | 0-1 |
| Ash, g/100 g | 5-10 |
| Total carbohydrate (by difference, g/100 g) | 45-60 |
| Calcium, mg/kg | 5000-6000 |
| Iron, mg/kg | 70-100 |
| Magnesium, mg/kg | 1700-2500 |
| Potassium, g/kg | 20-40. |

19. A method according to claim 18 wherein the sugar cane derived extract comprises the following:

| Component | |
|---|---|
| Polyphenols g CE/100 g | 1.15 |
| Moisture, g/100 g | 38.4 |
| Energy, (calc) kJ/100 g | 946 |
| Protein (N × 6.25, g/100 g) | 2.0 |
| Fat, g/100 g | 0.9 |
| Sucrose, g/100 g | 29.3 |
| Glucose, g/100 g | 5.4 |
| Fructose, g/100 g | 6.0 |
| Total sugars, g/100 g | 40.7 |
| Sodium, mg/10 g | 50 |
| Soluble dietary fibre, g/100 g | 0.3 |
| Ash, g/100 g | 6.1 |
| Total carbohydrate (by difference, g/100 g) | 52.3 |
| Calcium, mg/kg | 5450 |
| Iron, mg/kg | 89 |
| Magnesium mg/kg | 2000 |
| Potassium, g/kg | 24.5. |

20. A method for treating a subject having a condition associated with insulin resistance, or for a subject predisposed to a condition associated with insulin resistance, comprising the administration of a sugar cane derived extract enriched in polyphenols to the subject, wherein the administration of the sugar cane derived extract lowers postprandial glucose response and insulin response without leading to hypoglycaemia and wherein the sugar cane derived extract comprises the following:

| Component | |
|---|---|
| Polyphenals (g CE/100 g) | 4-8 |
| Moisture, g/100 g | 30-50 |
| Energy, (calc) kJ/100 g | 720-1030 |
| Protein (N × 6.25, g/100 g) | 0-3 |
| Fat, g/100 g | 0-0.5 |
| Sucrose, g/100 g | 10-20 |
| Glucose, g/100 g | 15-25 |
| Fructose, g/100 g | 15-25 |
| Total sugars, g/100 g | 40-70 |
| Sodium, mg/100 g | 1-10 |
| Soluble dietary fibre, g/100 g | 0-1 |
| Ash, g/100 g | 5-10 |
| Total carbohydrate (by difference, g/100 g) | 45-60 |
| Calcium, mg/kg | 500-600 |
| Iron, mg/kg | 7-10 |
| Magnesium, mg/kg | 170-250 |
| Potassium, g/kg | 2-4. |

21. A method according to claim 20 wherein the sugar cane derived extract comprises the following:

| Component | |
|---|---|
| Polyphenols (g CE/100 g) | 6 |
| Moisture, g/100 g | 40 |
| Energy, (calc) kJ/100 g | 900 |
| Protein (N × 6.25, g/100 g) | 0.5 |
| Fat, g/100 g | 0.1 |
| Sucrose, g/100 g | 15 |
| Glucose, g/100 g | 20 |
| Fructose, g/100 g | 20 |
| Total sugars, g/100 g | 55 |
| Sodium, mg/100 g | 5 |
| Soluble dietary fibre, g/100 g | 0.1 |
| Ash, g/100 g | 6.1 |
| Total carbohydrate (by difference, g/100 g) | 52.3 |
| Calcium, mg/kg | 550 |
| Iron, mg/kg | 8 |
| Magnesium, mg/kg | 200 |
| Potassium, g/kg | 2.45. |

22. A method for treating a subject having a condition associated with insulin resistance, or for treating a subject predisposed to a condition associated with insulin resistance, comprising the administration of a sugar cane derived extract enriched in polyphenols to the subject, wherein the administration of the sugar cane derived extract lowers postprandial glucose response and insulin response without leading to hypoglycaemia and wherein the sugar cane derived extract enriched in polyphenols comprises polyphenols in an amount of 4-8 g CE/100 g of extract.

23. A method for treating a subject having a condition associated with insulin resistance, or for treating a subject predisposed to a condition associated with insulin resistance, comprising the administration of a sugar cane derived extract enriched in polyphenols to the subject, wherein the administration of the sugar cane derived extract lowers postprandial glucose response and insulin response without leading to hypoglycaemia and wherein the sugar cane derived extract enriched in polyphenols comprises polyphenols in an amount of 6.5-13.5 g CE/100 g of extract.

* * * * *